(12) United States Patent
Bessette

(10) Patent No.: US 8,615,532 B2
(45) Date of Patent: *Dec. 24, 2013

(54) SYSTEM AND METHOD FOR ELECTRONICALLY MANAGING MEDICAL DATA FILES

(71) Applicant: Luc Bessette, Montreal (CA)

(72) Inventor: Luc Bessette, Montreal (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/628,182

(22) Filed: Sep. 27, 2012

(65) Prior Publication Data

US 2013/0024210 A1   Jan. 24, 2013

Related U.S. Application Data

(63) Continuation of application No. 13/162,054, filed on Jun. 16, 2011, now Pat. No. 8,296,333, which is a continuation of application No. 12/946,983, filed on Nov. 16, 2010, now Pat. No. 7,984,079, which is a continuation of application No. 12/771,055, filed on Apr. 30, 2010, now Pat. No. 7,856,456, which is a continuation of application No. 10/892,600, filed on Jul. 16, 2004, now Pat. No. 7,734,656, which is a continuation-in-part of application No. 09/735,585, filed on Dec. 13, 2000, now Pat. No. 6,775,670, which is a continuation-in-part of application No. 09/087,843, filed on May 29, 1998, now Pat. No. 6,263,330.

(30) Foreign Application Priority Data

Feb. 24, 1998 (CA) ........................................ 2231019
Apr. 1, 1998 (CA) ........................................ 2233794

(51) Int. Cl.
*G06F 17/30* (2006.01)

(52) U.S. Cl.
USPC ........... 707/803; 705/2; 455/3.01; 455/414.3; 709/203

(58) Field of Classification Search
USPC ................... 707/803; 705/2; 455/3.01, 414.3; 709/203
See application file for complete search history.

(56) References Cited

U.S. PATENT DOCUMENTS

| 4,893,270 A | 1/1990 | Beck |
| 5,715,823 A | 2/1998 | Wood |

(Continued)

FOREIGN PATENT DOCUMENTS

| CA | 2 366 300 A1 | 9/2000 |
| EP | 0 718 784 A1 | 6/1996 |

(Continued)

OTHER PUBLICATIONS

Akinyele, Joseph A. et al., "Securing Electronic Medical Records Using Attribute-Based Encryption on Mobile Devices", ACM, Oct. 17, 2011, pp. 1-12.*

(Continued)

*Primary Examiner* — Cheryl Lewis
(74) *Attorney, Agent, or Firm* — RatnerPrestia

(57) ABSTRACT

A network server arrangement including a processor with a machine readable storage encoded with software for execution by the processor. The network server arrangement is responsive to requests to access a medical record of an individual and generates summary medical record data including summary information having a plurality of data elements associated with the individual, at least one of the data elements conveying medical information about the individual, and a pointers component including at least one pointer pointing to a network location containing importable medical information in connection with the individual that is not contained in the summary information component. The pointer includes a machine readable address part for processing by the client, allowing the client to import the medical information from the network location, and a label part for displaying to a user the nature of the medical information residing at the network location.

36 Claims, 12 Drawing Sheets

(56) References Cited

U.S. PATENT DOCUMENTS

| | | | |
|---|---|---|---|
| 5,845,255 | A | 12/1998 | Mayaud |
| 5,884,246 | A | 3/1999 | Boucher |
| 5,903,889 | A | 5/1999 | delaHuerga |
| 5,918,010 | A | 6/1999 | Appleman |
| 5,924,074 | A | 7/1999 | Evans |
| 6,012,083 | A | 1/2000 | Savitzky |
| 6,018,713 | A | 1/2000 | Coli |
| 6,263,330 | B1 | 7/2001 | Bessette |
| 6,364,834 | B1 | 4/2002 | Reuss |
| 6,775,670 | B2 | 8/2004 | Bessette |
| 7,028,049 | B1 | 4/2006 | Shelton |
| 7,734,656 | B2 | 6/2010 | Bessette |
| 7,856,456 | B2 | 12/2010 | Bessette |
| 7,984,079 | B2 | 7/2011 | Bessette |
| 8,296,333 | B2 * | 10/2012 | Bessette ........................ 707/803 |
| 2004/0122787 | A1 | 6/2004 | Avinash |
| 2006/0136143 | A1 | 6/2006 | Avinash |
| 2006/0184489 | A1 | 8/2006 | Weiner |
| 2009/0164917 | A1 | 6/2009 | Kelly |
| 2010/0217619 | A1 | 8/2010 | Cox |

FOREIGN PATENT DOCUMENTS

| | | | |
|---|---|---|---|
| WO | WO 98/13783 | A1 | 4/1998 |
| WO | WO 98/20793 | A1 | 5/1998 |
| WO | WO 99/44162 | A1 | 9/1999 |
| WO | WO 00/57339 | A2 | 9/2000 |
| WO | WO 00/60435 | A2 | 10/2000 |
| WO | WO 02/03308 | A2 | 1/2002 |

OTHER PUBLICATIONS

Health Networking Solutions, Feb. 1998, http://k12.clearlake.ibm.com/healthcaresolution/hdnsol.html, Global Health Industry.

Janette Coble et al., Maintaining a Focus on User Requirements Throughout the Development of Clinical Workstation Software, Mar. 1997, pp. 1-10, http:www.acm.org/turing/sigs/sigchi/chi97/Proceedings/paper/jmc.html.

UPMC's Image Engine Project Expands Medical Records System; University of Pittsburgh Medical Center, Mar. 30, 1998, pp. 1-2, http://www.eurekalert.org/release/uptm-iepjemrs.html.

Henri J. Lowe, M.D., The Image Engine Project, Prototyping an Internet-Based Multimedia Electronic Medical Record System, 1997, pp. 1-37, http://www.pathology.pitt.edu/apiii97/talks/lowe/sld001.html.

Majorie Lazoff, M.D., Medical Records Projects, Feb. 1998, pp. 1-6, http://medicalcomputingtoday.com/onvemproj.html.

William M. Detmer, WWW and the Electronic Medical Record, Nov. 29, 1994, pp. 1-11, http://camis.stanford.edu./people/bdetmer/WW-WTalk/WWW-outline.html.

F.W. Stitt, World-WideWeb based Electronic Medical Records, Medix Software Systems, Key Biscayne, Florida USA, University of Miami School of Medicine, Miami, Aug. 1997, pp. 1-7, http://medixb.webnet.net/PAPER/apami.html.

Issac S. Kohane et al., Sharing Electronic Medical Records Across Multiple Heterogeneous and Competing Institutions, Proc AMIA Annual Fall Symposium, 1996, pp. 1-6.

K.E. Willard et al., W3 Based Medical Information Systems vs. Customer Client Server Applications, 1994, pp. 1-4, http://www.ncsa.uluc.edu/SDG/IT94/Proceedings/MedTrack/willard/UMHC__www/UMHC__paper.html.

TeleMed, Los Alamos National Laboratory, Mar. 1998, pp. 1-32, http://www.acl.lanl.gov/TelMed/.

David G. Kilman et al., An International Collaboratory Based on Virtual Patient Records, Aug. 1997, pp. 1-7.

David Forslund et al., The Virtual Patient Record: A Key to Distributed Healthcare and Telemedicine, Feb. 29, 1996, pp. 104, http://www.acl.lang.gov/TeleMed/Papers/virtual.html.

Grimson et al., Interoperability Issues in Sharing Electronic Healthcare Records—The Synapses Approach $3^{rd}$ IEEE International Conference on Engineering of Complex Computer Systems, Sep. 8-12, 1997, p. 180.

Grimson et al., Federated Healthcare Record Server—The Synapses Paradigm, International Journal of Medical Informatics, vol. 52, No. 1/03, pp. 3-27, Oct. 1, 1998.

Jagannathan et al., Corba-Based and Web-Based Patient Records Integration, Proceeding Towards an Electronic Patient Record Interntional Symposium on the Creation of Electronic Health Record System and Global Conference on Patient Record System and Global Conference on Patient Record, vol. 2, pp. 243-247, May 13, 1996.

Naslady et al., Patient Health Record on a Smart Card, International Journal of Medical Informatics, vol. 48, No. 1-3, pp. 191-194, Feb. 1, 1998.

Biskup et al., Cryptographic Protection of Health Information: Cost and Benefit, International Journal of Bio-Medical Computing, vol. 43, No. 1, pp. 61-67, Oct. 1, 1996.

Morger et al., Security Concerns for Mobile Information Systems in Health Care, $8^{th}$ International Workshop on Database and Expert System Applications, pp. 312-317, Sep. 1-2, 1997.

Li-Hsing Yen, Ting-Lu Huang, Shu-Yuen Hwang, A protocol for casually ordered message delivery in mobile computing systems, IEEE, 1997, pp. 365-372.

C.J. McDonald et al., The Regenstrief Medical Record System: a quarter century experience, International Journal of Medical Informatics 54, 1999, pp. 225-253.

Sittig, Dean F., Personal health records on the internet: a snapshot of the pioneers at the end of the $20^{th}$ Century, 2002, International Journal of Medical Informatics, Elsevier.

International Search Report dated Jul. 14, 1999.

Canadian Office Action for Canadian Patent Application No. 2,239,015 mailed Dec. 2, 2003.

USPTO Office Action of U.S. Appl. No. 10/892,600 dated Jun. 9, 2009.

Canadian Office Action for Canadian Patent Application No. 2,329,598 mailed Feb. 22, 2012.

Care Web™, Architecture, (Aug. 14, 1999), 1-2: http://clinquery.bidmc.harvard.edu/people/jhalamka/arch.html.

Chueh et al., Client-server, Distributed Database Strategies In a Health-care Record System for a Homeless Population, Journal of the American Medical Informatics Association, vol. 1, No. 2 ( Mar./Apr. 1994), pp. 186-198.

Australian Office Action received Sep. 21, 2006 for Australian Application No. 2002214873.

Forslund et al., Experiences with a Distributed Virtual Patient Record System, Proc AMIA Annual Fall Symposium (1996), pp. 483-487.

Halamka et al, A WWW Implementation of National Recommendations for Protecting Electronic Health Information, J AM Inform Assoc, vol. 4, No. 6 (1997), pp. 458-464.

Hurlen et al., Design and Functional Specification of the Synapses Federated Healthcare Record Server, Medical Informatics Europe-IOS Press (1997); pp. 334-338.

International Preliminary Examination Report for PCT/CA01/01549 mailed Jun. 17, 2003.

International Preliminary Examination Report for PCT/CA98/01198, mailed Mar. 28, 2000.

Kohane et al., Building National Electronic Medical Record Systems via the World Wide Web, Journal of the American Medical Informatics Association, vol. 3, No. 3 (May/Jun. 1996). pp. 191-207.

USPTO Notice of Allowance for U.S. Appl. No. 09/087,943 mailed Sep. 25, 2000.

USPTO Notice of Allowance for U.S. Appl. No. 09/735,585 mailed Mar. 22, 2004.

USPTO Notice of Allowance for U.S. Appl. No. 10/892,600 mailed Jan. 26, 2010.

USPTO Notice of Allowance for U.S. Appl. No. 12/946,983 mailed Mar. 9, 2011.

USPTO Non-Final Office Action for U.S. Appl. No. 09/087,843 mailed Feb. 14, 2000.

USPTO Final Office Action for U.S. Appl. No. 09/735,585 mailed Jun. 18, 2003.

USPTO Non-Final Office Action for U.S. Appl. No. 09/735,585, mailed Oct. 3, 2002.

USPTO Non-Final Office Action for U.S. Appl. No. 12/726,959 mailed Nov. 2, 2011.

(56) References Cited

OTHER PUBLICATIONS

European Office Action for EP 01 983 361.5 mailed Mar. 1, 2005.
European Office Action for EP 01 983 361.5 mailed May 23, 2007.
European Office Action for EP 98 963 301.1 mailed Jun. 22, 2006.
European Office Action for EP 98 963 301.1 mailed Mar. 7, 2001.
European Office Action for EP 98 963 301.1 mailed Jul. 27, 2007.
International Search Report for PCT/CA01/01549 mailed Apr. 28, 2003.
Wang et al., Dynamic Link Between ECG and Clinical Data by a CORBA-Based Query Engine and Temporal Mapping, Proc AMIA Annual Fall Symposium (1997), pp. 27-31.

* cited by examiner

CONFIDENTIAL MEDICAL FILE

LAST UPDATE: January 3 1998

SUBJECT: John Doe

IDENTIFIER: **  **

Go To:

| | |
|---|---|
| Administrative Medical Data: | Administrative |
| Permanent Biological Data: | Biological |
| Significant Antecedents: | Antecedents |
| Current Medical Condition: | Current |
| Links to Other Biological Data: | Other Links |

Administrative Medical Data
Back to Main Menu    Menu

HOME
Address:
Telephone:

WORK
Address:
Telephone:

EMERGENCY CONTACT
Name:
Telephone:
Relationship:

REGULAR PHYSICIAN
Name:
Telephone:
Relationship:

OTHER
Date of Birth:
Maiden Name of Mother:
Name of Father:
Status (Single or Married):
Name of Spouse (if applicable):

Permanent Biological Data
Back to Main Menu    Menu

Blood Type:
Genetic Markings or Deficiencies:
Tissue Antigens:

Figure 6B

Significant Antecedents
Back to Main Menu    Menu

PERSONAL MEDICAL HISTORY
Past Hospitalizations:
Major Treatments Incurred:

FAMILY HISTORY
Antecedents:

SURGICAL HISTORY
Antecedents:
Interventionist Radiology Procedures:
Genetic Alterations:
Summary of Past Operation Protocols and Procedures:

Current Medical Condition
Back to Main Menu    Menu

Allergies:
Medication(s) Used:

Links To Other Biological Data
Back to Main Menu    Menu

MOST RECENT CORONAROGRAPHY      PREVIOUS CORONAROGRAPHIES
MOST RECENT ELECTROCARDIOGRAM   PREVIOUS ELECTROCARDIOGRAMS
MOST RECENT X-RAY               PREVIOUS X-RAYS
MOST RECENT BRAIN CT SCAN       PREVIOUS BRAIN CT SCANS

Figure 6C

SYSTEM AND METHOD FOR ELECTRONICALLY MANAGING MEDICAL DATA FILES

CROSS REFERENCE TO RELATED APPLICATIONS

The present application is a Continuation Application of U.S. patent application Ser. No. 13/162,054 filed on Jun. 16, 2011 which issued as U.S. Pat. No. 8,296,333 on Oct. 23, 2012 which is a Continuation Application of U.S. patent application Ser. No. 12/946,983 filed on Nov. 16, 2010 which issued as U.S. Pat. No. 7,984,079 on Jul. 19, 2011 which is a Continuation Application of U.S. patent application Ser. No. 12/771,055 filed on Apr. 30, 2010 which issued as U.S. Pat. No. 7,856,456 on Dec. 21, 2010 which is a Continuation Application of U.S. patent application Ser. No. 10/892,600 filed on Jul. 16, 2004, which issued as U.S. Pat. No. 7,734,656 on Jun. 8, 2010 which is a Continuation-In-Part Application of U.S. patent application Ser. No. 09/735,585 filed Dec. 13, 2000, which issued as U.S. Pat. No. 6,775,670 on Aug. 10, 2004, which is a Continuation-In-Part of U.S. patent application Ser. No. 09/087,843 filed May 29, 1998, which issued as U.S. Pat. No. 6,263,330 on Jul. 17, 2001.

FIELD OF THE INVENTION

The present invention relates to the field of information distribution systems. More specifically, the invention pertains to a system and method for the electronic management of medical data files, enabling complex genetic research to be conducted on the medical data contained in those files.

BACKGROUND OF THE INVENTION

In the past few years, the worlds of information and technology have made important evolutions. We have progressed from a universal analogical support, usually on paper, towards a theoretically universal electronic support based on the multimedia as well as Internet Protocol (IP) based technology such as the World Wide Web (WWW), JAVA™ and ICQ™ (I Seek You). The transmission of information has also made tremendous progress and is already, or will be soon, practically instantaneous no matter the form of information: text, data, sound, fixed or animated image.

The search for information is becoming more and more similar to the concept of navigation among diverse sources of information and even within documents themselves. The concept of navigation itself implies the need for user accessible tools as well as some sort of structured organization.

Narrowing the focus, this major revolution of information systems brings about profound changes in the relations between academic and hospital domains, in particular everything which deals with medical archives and databases as well as the ability to consult aggregates of these in a transparent way and to share in real or delayed time the information obtained. The number of information sources is multiplying and the to communication networks are proliferating: more and more documentation is available in digital form and the information highway is rapidly expanding. Concerning medical archives and databases, questions arise as to their role of maintaining or distributing information. If their roles of acquiring, cataloging, and maintaining information are to continue, they will have to give access to the available information on new multimedia supports as well as serve as access points to the information within enlarged networks (e.g., the Healthcare Inforoute™). These changes will add to the complexity of their management, all the while enlarging their traditional mandate.

In other words, the medical archives and databases of the future will not only be locally archived medical-legal clinical documents, but also high-performance data banks of primary importance to the practice of medicine and health care everywhere within our network, all the while constituting a living core dedicated to clinical and scientific research and development.

The above described evolution of the medical file and database system requires that the following two objectives be achieved:
  effective navigation across multiple and diverse sources of information, both local and distant, performed in a transparent way with respect to the end user; and
  efficient file management allowing universal research, the treatment of contained information, and the sharing of information between system users.

Currently, in order to store medical archives and databases, passive data accumulation for each medical facility takes place within a local network. Unfortunately, the costs of stocking information and storing files in a local network are quite high and the space available is limited. There is also a well-established historical insufficiency concerning the ability of the local medical archive file networks to respond to the documentary and informational needs of the emergency doctor, the consultant, the bio-statistician, or the genetic researcher. The medical facilities do not have access to a complete ensemble of information sources, thus complicating emergency medical procedures and diagnoses all the while hampering the facility's ability to give patients the most appropriate treatment.

Although the solution of combining the multiple independent local networks into a single integrated health network seems viable, the implementation of such a concept presents certain problems concerning the manner in which medical data is currently recorded and treated, at both text and image levels. First of all, each separate medical facility may count up to hundreds of thousands of active files, some archived locally, others externally, either in an integrated or a refined form. Second of all, the file organization may be different at each facility, which is a huge obstacle to the merging of all files into a system that supports a common format file organization. There is also the problem of available space when considering the large volume of information contained in each file and the fact that the life of a particular medical file may approach up to twenty-five years in length. Thus volume and merging problems lead to the conclusion that it is currently almost impossible to combine and digitize the whole of all local medical records from all local networks.

Even if the merging and digitizing were possible, there is a question as to whether this would be desired. The data recorded in the medical files does not all have the same informational and discriminatory value in the long run. In fact, the data falls into three categories: data with strict medical-legal value, data with short-term clinical value, and data with historical value or a biological signature. Unfortunately, the first category, data with strict medical-legal value, makes up the majority of data recorded in the file while it represents the least valuable information for emergency doctors, consultants, bio-statisticians, and genetic researchers. On the other hand, the most valuable information for emergency procedures and diagnoses, the third category, makes up a very small portion of data recorded in the file. Therefore, an integrated file management system which combines all of the information currently held in archived medical files would be extremely inefficient in terms of usage of space, thus impairing the extraction of information pertinent to a particular research.

It is therefore desirable to provide a method for developing the information highway to allow for access to shared medical files in an enlarged health network and other external databases in order to increase the number of available sources of information for doctors and consultants.

Such an enlarged health network may potentially contribute to advancements in genetic research, which is currently in its early stages of development. In particular, genetic researchers engaged in the identification of links or associations between an individual's genetic data and medical disease outcomes require much information to carry out their studies. As such, a regularly updated database of genetic and medical information would be a potential gold mine of data to these researchers.

An existing method for identifying associations between genetic data and medical disease outcomes is to conduct an epidemiological study. Epidemiology is a branch of medical science that deals with the incidence, distribution, and control of disease in a population. Epidemiological studies include, but are not limited to, case control studies, cohort studies, prospective, retrospective, and longitudinal studies.

In a case control study, people having a disease of interest are identified, then compared with a suitable control group of people without the disease. A cohort study involves two groups (cohorts) of patients, one of which received the exposure of interest and one of which did not. Both groups in the cohort study are studied for the outcome of interest. In a prospective study, subjects are followed from a given point in time and into the future, whereas in a retrospective study, outcomes have occurred to the subjects before the study has even commenced. Finally, a longitudinal study is a study in which the same group of individuals is interviewed at intervals over a period of time.

It is apparent that any one of these different types of epidemiological studies involves a limited number of subjects, which in turn limits the amount of data that can be obtained for research purposes. Furthermore, not only is the pool of data restricted by the number of people participating in a study, but also by the amount of genetic and medical data that can feasibly be obtained for each participant. It is noted that acquiring genetic data is a relatively complex and expensive task. Moreover, because the subjects in an epidemiological study must be observed and often followed over a period of time, this method of research is time consuming and requires a considerable amount of human resources.

Thus, a need clearly exists for a system and method of electronically managing medical data files, in order to facilitate research on the associations between genetic data and medical disease outcomes.

SUMMARY OF THE INVENTION

In a broad aspect, the present invention is directed to a method for conducting genetic research on medical data. The method includes the step of accessing a database storing a plurality of medical records associated with a plurality of individuals, each medical record including at least one unique identifier associated with a certain individual and medical data associated with the certain individual. The method also includes the steps of extracting from the database the medical data associated with at least a subset of the plurality of individuals and, for each individual of the subset, obtaining electronically stored genetic data associated with the respective unique identifier. Also, the method includes processing the extracted medical data and obtained genetic data for attempting to identify an association between particular genetic data and a particular medical condition.

In another broad aspect, the invention provides a method for conducting genetic research on medical data of a network system. The network system includes at least one server managing a database, the database containing a plurality of medical records associated with respective individuals, each medical record including at least one unique identifier associated with a certain individual and a collection of medical data elements associated with the certain individual, the collection of medical data elements including genetic data and health status information. The method includes the steps of accessing at least a subset of the medical records stored in the database and extracting the genetic data and health status information from the subset of medical records. The method also includes the step of providing the extracted genetic data and health status information to an adaptive expert system capable of processing the extracted genetic data and health status information in order to attempt to identify an association between particular genetic data and a particular medical condition.

In yet another broad aspect, the present invention is directed to a combination of a network server having a first database storing a plurality of medical records associated with respective individuals, a second database storing a plurality of medical files associated with respective individuals, and an adaptive expert system. Each medical record of the first database has at least one unique identifier associated with a certain individual and a collection of medical data elements associated with the certain individual, the collection of medical data elements including health status information. Each medical file of the second database has at least one unique identifier associated with the respective individual and genetic data associated with the respective individual. The adaptive expert system can extract from the first and second databases the health status information and genetic data associated with at least a subset of individuals, and is operative to process the extracted genetic data and health status information in order to attempt to identify an association between particular genetic data and a particular medical condition.

BRIEF DESCRIPTION OF THE DRAWINGS

These and other features of the present invention will become apparent from the following detailed description, considered in connection with the accompanying drawings. It is to be understood, however, that the drawings are provided for purposes of illustration only and not as a definition of the boundaries of the invention, for which reference should be made to the appending claims.

FIGS. 6A, 6B, and 6C represent the NDSMR document layout in accordance with an embodiment of the present invention;

DETAILED DESCRIPTION OF THE INVENTION

Figure 1:
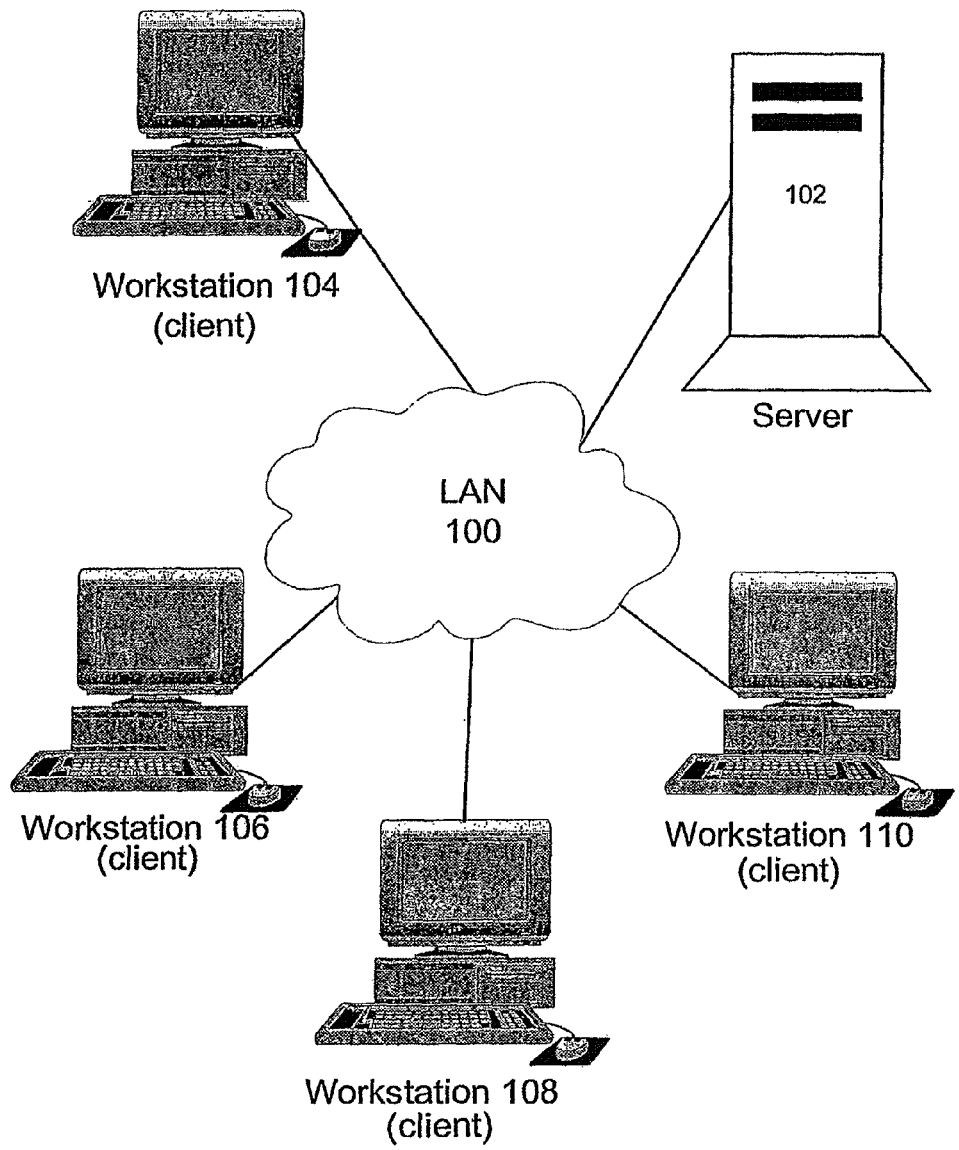
FIG. 1 is a block diagram of a generic client-server environment, where clients and server are linked by a local area network (LAN)

FIG. 1 illustrates a generic client-server environment, enabled by a local area network (LAN) 100. Client-server computing is a cooperative relationship between one or more clients and one or more servers. The clients 104, 106, 108, and 110 submit requests to the server 102, which processes the requests and returns the results to the clients. Although the processing is initiated by the client(s), both client(s) and server cooperate to successfully execute an application. Therefore, the interaction between the client and the server processes is a transactional exchange in which the client is proactive and the server is reactive. In addition to client(s) and server, the third essential component of the client-server environment is the network. Client-server computing is distributed computing. In other words, users, applications, and resources are distributed in response to business requirements and are linked by a single LAN 100 or by an Internet of networks.

Currently, most medical facility archives still operate on a paper-based support system. The higher-end medical facilities are set up with their own LAN for archiving medical files, however, and the computing system is often modeled after the client-server system shown in FIG. 1. Since each separate facility has its own LAN for archiving files, the accessibility to files of a particular LAN is limited to the workstations linked to that particular LAN.

Figure 2:
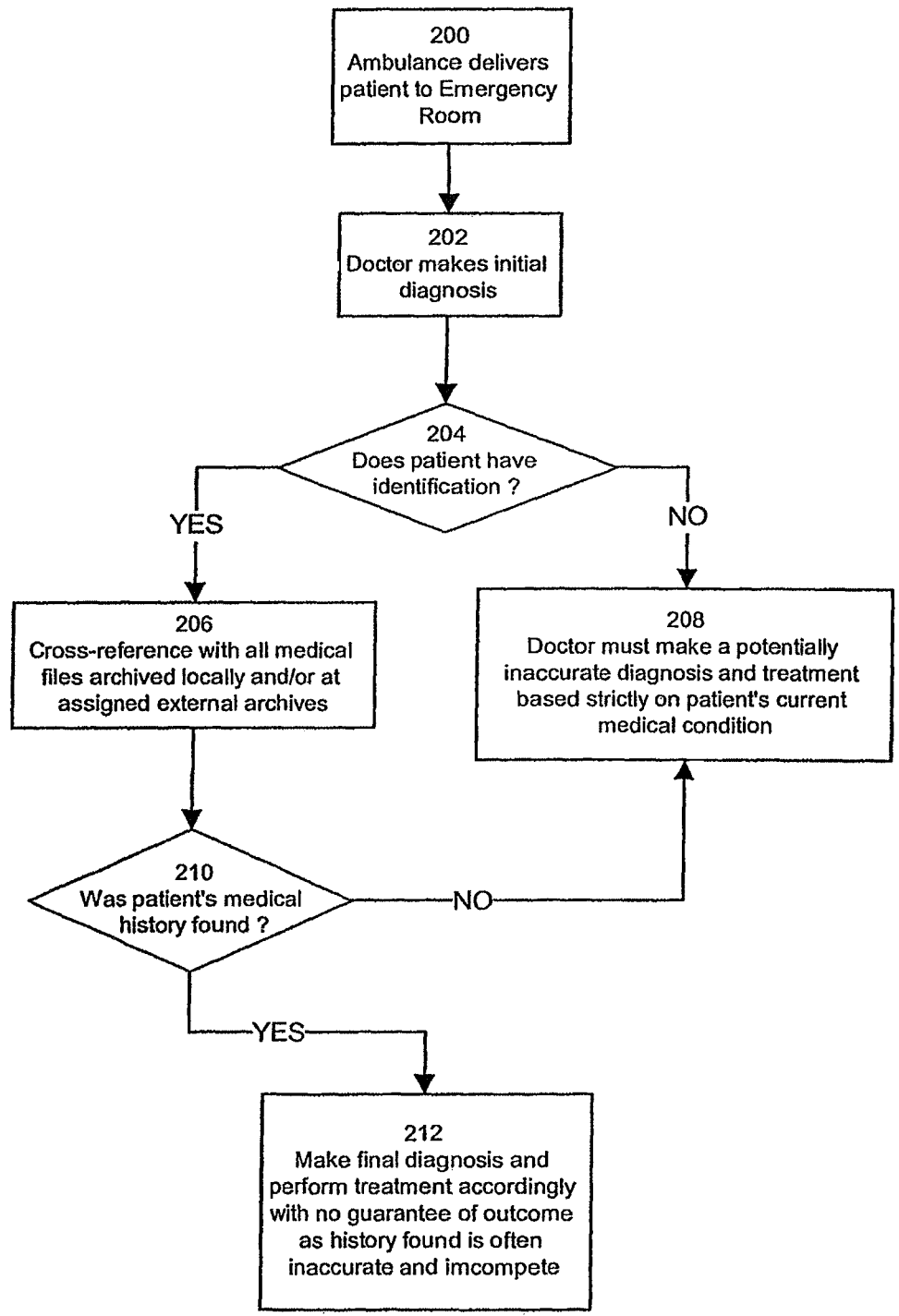
FIG. 2 is a flowchart depicting the current diagnostic process that takes place in medical facilities.

FIG. 2 depicts an example of the current state of affairs faced by medical facilities. Assume an ambulance delivers an unconscious patient to the emergency room (ER) at step 200. At step 202, the doctor makes an initial diagnosis, but needs access to the patient's medical history in order to prevent any misdiagnosis. If the patient is without identification of any kind, a question asked at step 204, the doctor has no other recourse but to administer a treatment at step 208 based on a diagnosis that is potentially inaccurate because it has been established strictly on the patient's current medical condition, without taking into account his/her previous medical history. If the patient does have an identification of some kind, it can be used to cross-reference all of the hospital's medical files, archived locally and/or at assigned external archives, at step 206. The patient's file will only be found, at step 210, if the patient was previously treated at the same hospital and already has a file stored in the network server's database. If the file is not found, the doctor is back to step 208. Even if the file is found, it is often incomplete and inaccurate as it lacks the information concerning treatment(s) administered in other medical facilities. Therefore, at step 212 the doctor must make a final diagnosis and perform the corresponding treatment.

Figure 3:
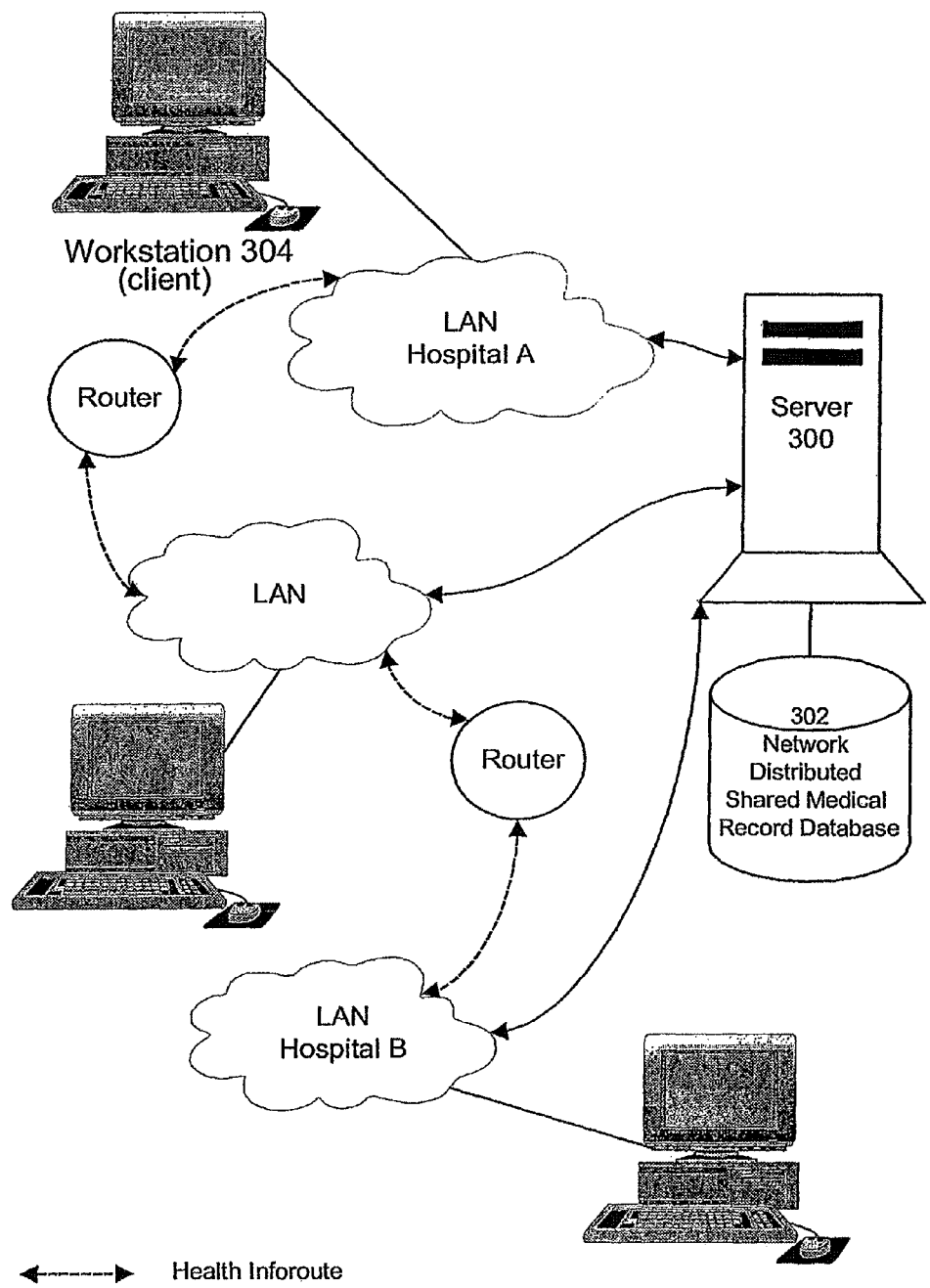
FIG. 3 is a block diagram of the health inforoute integrated with the Network Distributed Shared Medical Record (NDSMR) System, in accordance with an embodiment of the present invention.

FIG. 3 depicts an integrated health network embodying the principles of this invention. For the purposes of this specification, the word "integrated" implies the implementation of internetwork communication between all of the various medical facility LANs, each having one or more client workstations 304, as well as with external sources such as the global Internet, the pharmaceutical network, on-line medical libraries and journals, among many other possibilities. An important component of this network is a Network Distributed Shared Medical Record (NDSMR) system that includes two main components, a server 300 and a NDSMR database 302, with the potential for each LAN within the health network to be connected to the server 300. Alternatively, the system may include more than one server, all operating intercooperatively in order to manage the NDSMR database, a resource shared by all of the servers. Although such integrated medical networks may be restricted to a particular geographical region, due to differing medical jurisdictions within a country or between different countries, it is an integration hurdle which could eventually be overcome as a result of a concept of the current invention known as an individual's biological signature, to be described in detail below. The integration of medical facilities could thus someday be national wide, or even international wide, thereby enlarging and improving the health network.

Figure 4:
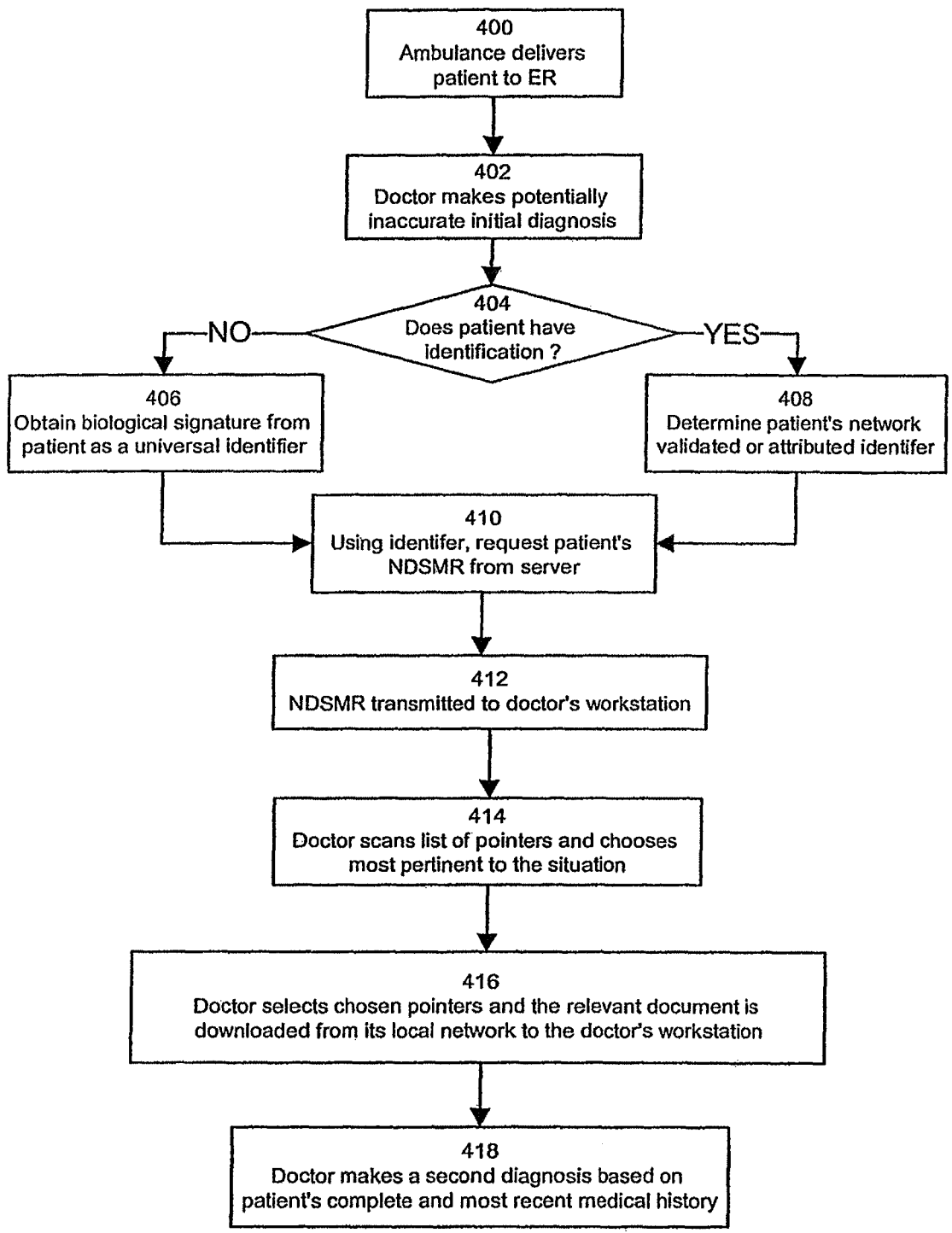
FIG. 4 is a flowchart depicting the diagnostic process which will take place in medical facilities under the NDSMR System, in accordance with an example of implementation of the present invention.

FIG. 4 is a flowchart depicting the improved diagnosis process as a result of the present invention. Assume that an ambulance delivers an unconscious patient to Hospital A at step 400. Also assume that the patient is a network user of the health network, and therefore has a personal file stored in the NDSMR database. After the doctor makes an initial diagnosis at step 402, the patient is checked for identification at step 404.

If the patient does have identification, his/her network validated or attributed identifier will be known at step 408. In the most preferred embodiment of this invention, such an identifier consists of the patient's medical insurance number such as the one available in a number of countries of the world, including Canada. Alternatively, the identifier may consist of the patient's social insurance number, Smart Card, or any other network-attributed identification. A Smart Card is an integrated circuit-based card containing individual specific medical information, to be read from and written to by appropriate electronics, and offers several implementation alternatives to the NDSMR system, to be described in more detail below. If the patient does not have identification, his/her biological signature can be obtained as a universal identifier at step 406. In a particular example of implementation of this invention, such an identifier consists of a fingerprint-derived signature. Different types of software-based technology for the implementation of system user identification via a fingerprint-derived biological signature exist and are currently available on the marketplace. Alternatively, the identifier may consist of a patient's retinal or genetic-derived signature, or any other type of biological signature.

At step 410 the doctor sits down at workstation 304 and logs onto the server 300, as will be discussed below. When prompted, the doctor uses the identifier obtained at either step 406 or step 408 in order to request the patient's NDSMR from the server 300. The record is transmitted from the NDSMR database 302 to the doctor's workstation at step 412. Once the doctor has read the pertinent medical information found in the record, he/she can scan a list of pointers appended to the record. As will be further described below, these pointers represent various significant medical documents (such as x-rays, surgical reports, etc.), and by their textual or visual representation allow the doctor to determine which of the pointers refer to documents pertinent to the patient's current medical condition. Specific to this example, the doctor decides at step 414 that a pointer referring to the most recent electrocardiogram taken at Hospital B would be helpful for diagnosis, and at step 416 he/she activates the corresponding pointer. Consequently, the document is downloaded over the health network from Hospital B's LAN to the doctor's workstation. This document allows the doctor to make a second diagnosis based on the patient's complete and most recent medical history at step 418.

Figure 5:
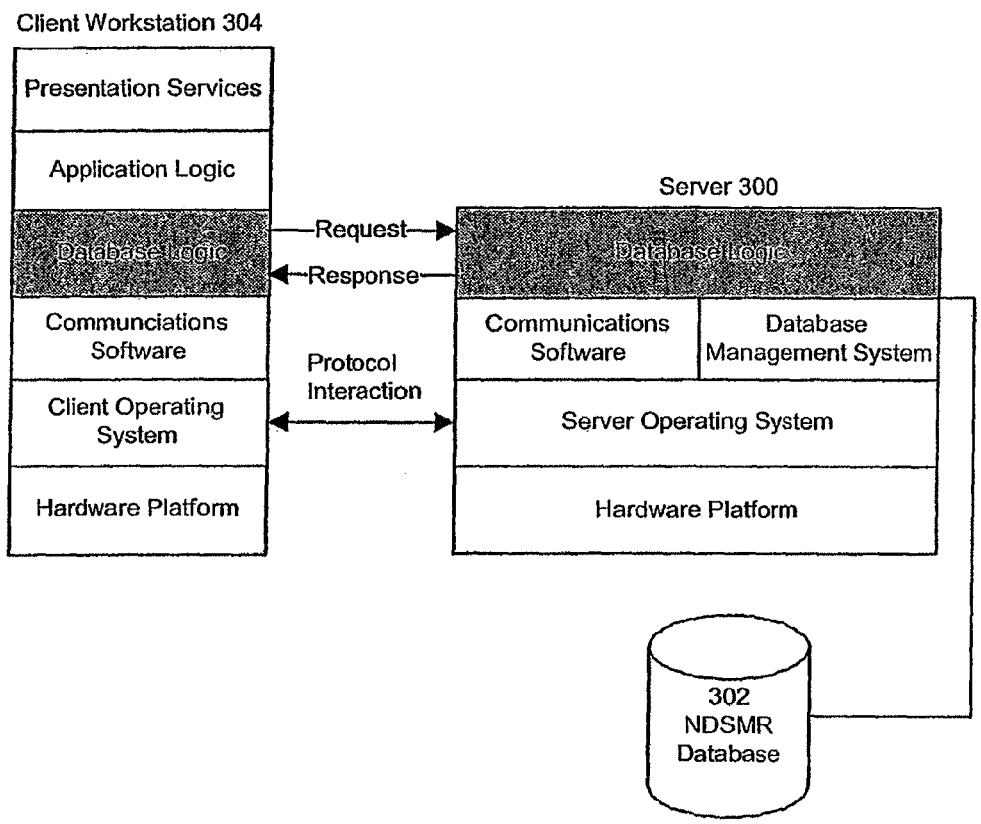
FIG. 5 is a block diagram of a general client-server architecture.

FIG. 5 is a general representation of the client-server architecture that implements the NDSMR system. The system includes three main components, notably the client 304, the server 300, and the NDSMR database 302. In both client 304 and server 300, the basic software is an operating system running on the hardware platform. The platforms and the operating systems of the client and server may differ. Indeed, a key component of the NDSMR system is that through client-server computing a multitude of different types of operating systems may exist within the various medical facility LANs. As long as the client 304 and server 300 share the same communication exchange protocols and support the same applications, the lower-level differences are irrelevant. It is the communications software which enables clients and server to interoperate. Specific to the NDSMR system, the communication exchange protocol adopted will be an open, non-proprietary protocol, for instance the Internet Protocol, a standard exchange protocol in client-server networking, or any other similar progressive communication exchange protocol.

For the purpose of this specification, the term interoperate implies, among other things, the ability of different system users (clients) to share server information and have on-line consultations, in both real and delayed time. Real-time computing is defined as the type of computing in which the correctness of the system depends not only on the logical result of the computation but also on the time at which the results are produced. Real-time tasks therefore attempt to control or react to events that take place in the outside world. As these events occur in "real time," a real-time task must be able to keep up with the events with which it is concerned. On the other hand, delayed-time tasks are not at all concerned with the outside world events, delayed-time system correctness depending solely on the logical result of the computation.

The benefits of real-time medical consultations in the case of emergencies are very clear. For example, consider a doctor at Hospital C conferring with a doctor at Hospital D that is remote from Hospital C. Both doctors can share access to an individual's NDSMR, simultaneously studying the record, visible on both of their workstations, and communicating in real-time with each other via some sort of text, voice, or video communications link, for instance an Internet messaging window, from their workstations. The equipment necessary to allow for such real-time communication will not be described in detail, as there are a variety of products available on the market that could be used for this task and that are well-known to persons skilled in the art.

The server 300 is responsible for maintaining the NDSMR database, for which purpose a database management system module is required. A variety of different applications that make use of the database may be housed on the client machines. The operative relationship that ties clients, such as client 304, and server 300 together is software that enables a client to make requests to the server 300 for access to the NDSMR database 302. It is important to note that the division of work between a client 304 and server 300 may be allocated in a number of ways. In a preferred embodiment of this invention, the system implements cooperative processing, whereby the application processing is performed in an optimized manner by taking advantage of the strengths of both client and server machines and of the distribution of data. Although such a configuration is quite complex to set up and maintain, in the long run this configuration offers greater user productivity gains and greater network efficiency.

Alternatively, the system may be implemented with server-based processing or client-based processing. In server-based processing, the most basic class of client-server configuration, the client is mainly responsible for providing a user-friendly interface, whereas nearly all of the processing is done on the server. In client-server processing, virtually all of the application processing is done at the client, with the exception of certain data validation routines and other database logic functions that are best performed at the server. This latter architecture is perhaps the most common client-server approach in current use. In the interest of clarity, the server-based processing implementation is described in the remainder of this description; however, the NDSMR client-server division of work may be any one of the options described above.

Figure 7:
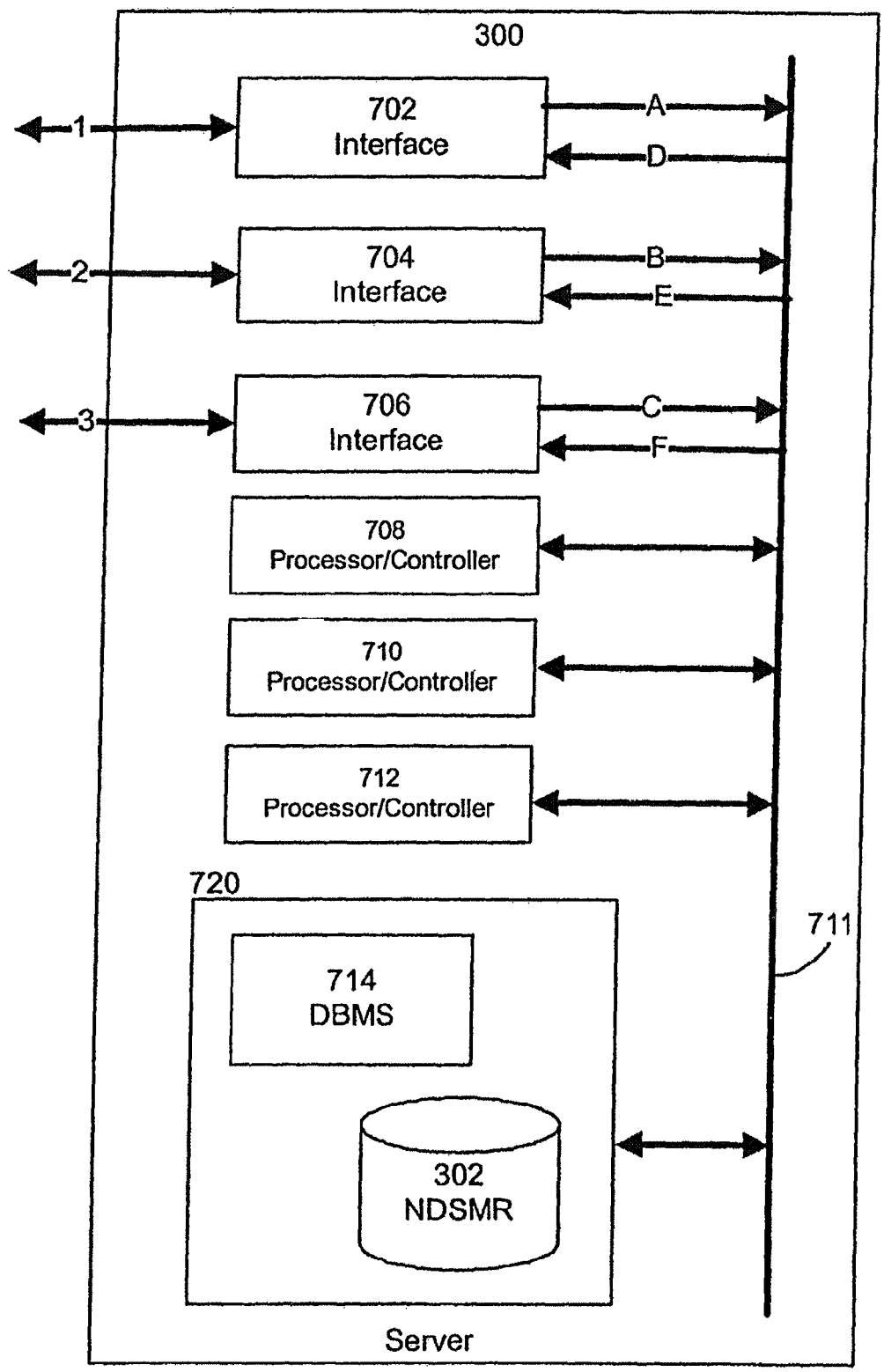
FIG. 7 is a block diagram of a server in accordance an embodiment of the present invention.

FIG. 7 is a more detailed block diagram of a preferred embodiment of the server 300, which has the responsibility of managing, sorting, and searching the NDSMR database 302. Towards this end, the server is provided with a memory 720, high-speed processor/controllers 708, 710, and 712 (assume for this example that there are three), and a high-speed input/output (I/O) architecture. The I/O architecture consists of the interfaces 702, 704, and 706. An internal system bus 711 interconnects these components, enabling data and control signals to be exchanged between them. The server has 6 ports, identified as port A, port B, port C, port D, port E, and port F. These ports connect the server to physical links 1, 2, and 3, allowing data to be transported to and from various clients within the network. In the example shown, ports A, B, and C are input ports on the physical links 1, 2, and 3, respectively, while ports D, E, and F are the output ports on those same physical links. The input ports are designed to receive data from their associated physical links, while the output ports are designed to transmit data over their associated physical links.

The interfaces 702, 704, and 706 interconnect various input and output ports to the physical links 1, 2, and 3, respectively. Their function is to transmit incoming data packets to the internal system bus 711 for transport to the memory 720 where they can be processed by one of the processors. On the output side, the interfaces are designed to accept data packets from the system bus 711 and impress the necessary electrical signals over the respective physical links so that the signal transmission can take effect. It is not deemed necessary to discuss this standard operation of the interfaces 702, 704, and 706 in more detail because it is well known to those skilled in the art and is not critical to the success of the invention.

The memory 720 contains a program element that controls the operation of the server. That program element is comprised of individual instructions that are executed by the controllers, as will be described in detail below. The program element includes several functional blocks that manage several tasks. One of those functional elements is the Database Management System (DBMS) 714 which provides efficient and effective use and maintenance of the NDSMR database 302. The DBMS will not be described in detail because it is well known to those skilled in the technological field to which the present invention belongs.

Besides the program element, the memory also holds the usual routing table that maps the destination addresses of incoming IP data packets (inherent to the IP communications exchange protocol) to the server output ports. It is not deemed necessary to discuss the structure of the routing table here because this component is not critical for the success of the invention and also it would be well known to a person skilled in the technological field to which the present invention belongs. The memory also provides random access storage, capable of holding data elements such as data packets that the processors manipulate during the execution of the program element.

Another component stored in the memory 720 is a validation table, which maps all of the registered user IDs to corresponding passwords. The table is used to validate clients logging on to the server, for security purposes. One of the characteristics of cooperative or client-based processing is that a system feature such as user validation would not necessarily be exclusive to the server, but could also take place, in whole or in part, at the client workstation. This would remove from the server a part or all of the burden of dealing with invalid clients, thus increasing system speed and efficiency. The identification table associates with each user a unique user profile that specifies permissible operations and NDSMR accesses, in order to limit access to data held within the database. Specifically, the table is used to identify between clients with different user privileges, for instance clients with archivist status as opposed to basic user status. Archivist status accords the client with read and write status, including editing and modifying privileges, for updating the NDSMRs. User status limits the client to NDSMR read status only. Finally, the memory 720 contains a request queue which is a buffer memory space of the FIFO type, although alternative types of buffer memory space may also be used, that can hold data packets to be sent to one of the controllers for processing. The physical configuration of the buffer does not need to be described in detail because such a component is readily available in the marketplace and the selection of the appropriate buffer mechanism suitable for use in the present invention is well within the ability of a person skilled in the art.

In a most preferred embodiment of this invention, the NDSMR database 302 is part of the memory 720 of the server 300, as shown in FIG. 7. In this embodiment, the NDSMR database 302 is actually on a separate storage medium, such as a non-volatile medium interconnected through a high-speed data bus with the memory 720 so the record set from the database 302 can be quickly loaded in the random access memory 720 for processing. Alternatively, the collection of data which makes up the NDSMR database 302 may be stored remotely on one or a set of physical storage device(s), for instance a disk. In such a case, one of the server's device drivers would be responsible for communicating directly with the peripheral device(s) in order to access the database.

Figure 8:
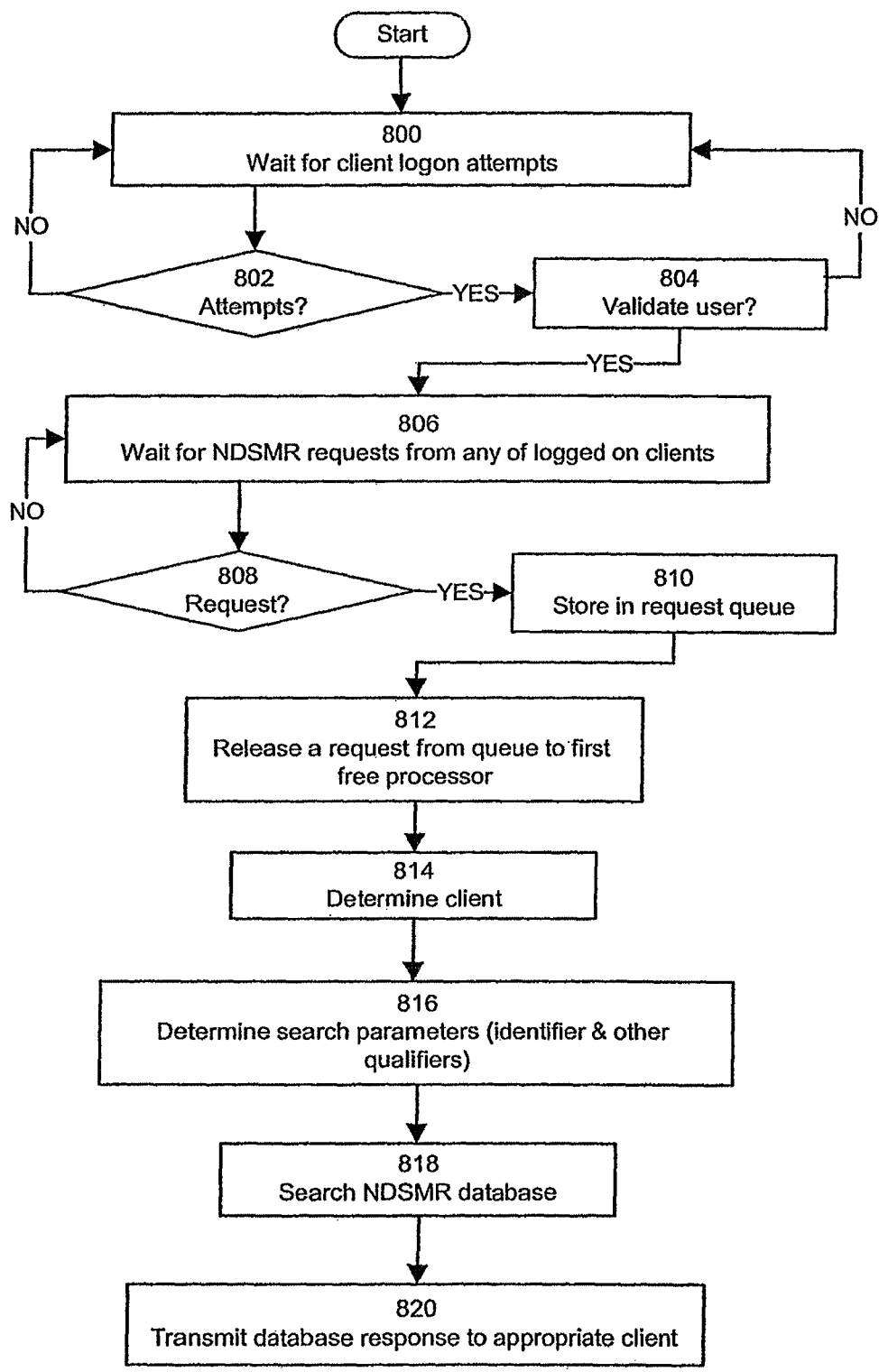
FIG. 8 is a flowchart illustrating the operation of a program element in the server shown in FIG. 7, in accordance with an example of implementation of the present invention.

FIG. 8 provides a complete flowchart illustrating an example of the operation of the program element stored in the memory 720, and executed by any one of the processor/controllers, that regulates the operation of the server 300, specifically its interaction with the clients as well as with the NDSMR database 302. Although the server program is running at all times, if no clients are logged on to the server then it is in an effective perpetual wait state, shown at step 800. Once a client attempts to log on, at step 802, control is passed to the validation functional block that is part of the program element in order to ensure that the client is a server-registered user at step 804. Validation consists simply in ensuring that the user's ID is known to the system (exists within the validation table) and that the user knows the correct password associated by the system with that ID (mapped by the validation table). If either the user's ID is not known to the system, or the password given is incorrect, validation will fail and the user refused possibility of logging on to the server. This is a basic validation procedure that is widely used. More complex validation methods can be implemented if the level of security demands it.

Next, the server waits for a request from any of the logged on clients at step 806. When a request does occur, it arrives as a flow of data packets at interface 702, 704, or 706, over physical link 1, 2, or 3, respectively. The request is confirmed at step 808. At step 810, the request is stored in the request queue found in memory 720, to await its turn for processing. The program element next releases a request from the queue (the oldest request) to any non-busy processor. If all of the processors are occupied, the release step 812 is delayed until one of the three processors is available.

Once a request has been released to a processor, the program element reaches step 814, whereby the requesting client is identified by the identification logic stored in memory 720. The identification logic first reads the request data packet header in order to determine the destination address for the response to the request, specifically the address of the requesting client which is read from the source field, and second assigns correct status to the client (user, archivist, or other status). This status is determined by the user profile, read from the identification table stored in memory 720. Step 814 also includes routing logic, whereby the routing table is accessed in the memory 720 in order to determine the correct output port for transmitting a database response to the particular client.

At step 816, the processor must determine the search parameters specified by the request. These parameters consist of a patient's identifier and/or a list of other qualifiers (for instance a particular treatment, medical condition, age group, sex, etc). Control is passed to the DBMS logic at step 818, at which point the search is performed on the NDSMR database. The DBMS not only performs the search on all data contained within the NDSMR database, but also controls access to specific records or even portions of records within the database, ensuring that confidential data or specific confidential parts of the data being accessed are masked when returned to the client, based on the user profile determined at step 814. The data returned by the NDSMR database search are transmitted over the pre-determined output port and to the appropriate client at step 820.

As indicated above, an aspect of the current invention is the user-friendly interface provided at the client workstation 304. This interface facilitates the user's attempts at making requests of the server, through easy-to-follow prompts and an on-line knowledge system to help the user with any questions or problems. The interface allows the user to perform searches or queries on the NDSMR database, using information filters to simplify the extraction of pertinent data from what may be hundreds of thousands of network-distributed shared medical records.

The interface also allows the user to perform keyword-based Internet-wide searches, transparent to the user. For example, a workstation user could initiate an Internet search for all documents relating to a particular medical condition by simply inputting the name of the medical condition as the keyword, the search results returned to the user being a list of hypertext links to all corresponding Internet documents. Note that different software packages for implementing such an interface feature exist and are currently available in the marketplace.

Finally, the interface offers text-processing tools, necessary to the editing, publishing, and merging of all data received from both the Internet and the server 300. Future variations to the NDSMR system may include a more progressive interface at the client workstation. Specifically, a three-dimensional view of the human body may be available to doctors and consultants logged on to the NDSMR server, used for making requests, medical enquiries, and searches.

The Network Distributed Shared Medical Record itself is another element. The NDSMR is an evolving summary medical document for a particular individual, integrated in the form of a network accessible document. By "summary" it is meant that the record does not necessarily contain all the information currently found in local network medical archives. Rather, the record is a compendium of critical medical information pertinent to a particular individual, potentially useful in the medical diagnosis of an individual's state of health and corresponding treatment. The NDSMR is therefore a shared minimal record, offering a common communication interface to medical facilities that may be using incompatible information systems. It has the merit of being able to be consulted easily, at a distance, on an emergency basis, as opposed to the current situation of files archived in a local network but inaccessible to any users in other networks.

In a preferred embodiment of this invention, the NDSMR includes at least one universal or network-attributed identifier, distinguishing one record from another, and a dynamically updated list of biological data pertinent to the individual, accessible by pointers referring to the local network where the data is actually being stored. This biological data consists of significant medical documents in an electronic format such as laboratory tests, x-rays, surgical reports, electrographic data, etc. Alternatively, other embodiments of the NDSMR may also include a variety of other medical information pertinent to the individual.

Figure 6A:

FIGS. 6A, 6B, and 6C display a possible layout for the NDSMR as a WWW document, presenting several categories of medical information pertinent to an individual, in this example John Doe. The individual's identifier is indicated at the top of the record, as seen in FIG. 6A. FIGS. 6B and 6C display other categories of information, including:

- administrative medical data (date of birth, home and work address and phone number, emergency contact, regular physician, etc.);
- permanent biological data (blood type, genetic markings or deficiencies, tissue antigens, etc.);
- significant antecedents (family medical history, personal medical history, surgical history, etc.); and
- current medical condition (allergies, medication, etc.).

The final category seen in FIG. 6C consists of the dynamically updated links to other biological data. The eight pointers listed refer to other medical documents pertinent to John Doe which are maintained in different local networks, and which can be downloaded from another network site to the client workstation by invoking the downloading operation embedded in the pointer, thus specifying the address of the site (and if necessary of a particular file at that site).

In addition to the set of pointers, the NDSMR could also offer access to complementary external sources of information, transparent to the workstation client. Potential sources could be pharmacy networks, medical libraries or journals, accessible to the doctor or consultant via references within the NDSMR seen on their workstation. Assume a consultant has downloaded John Doe's NDSMR from the server 300, and is verifying the Medication(s) Used reference under the Current Medical Condition category, seen in FIG. 6C. When the consultant invokes the Medication(s) Used reference, for instance by clicking with the computer mouse on the hypertext link, the NDSMR system will automatically generate user authorization in order to access an Internet published Medical Library that may be held on an Internet site containing this information, thus allowing the consultant to look up the specifics concerning John Doe's current medication.

In accordance with this invention, the data structure of the pointer allows the workstation user, such as a doctor or consultant, to determine the general nature of the information to which the pointer is referring. In other words, the doctor can tell by simply looking at the pointer whether it points to a medical document concerning a pulmonary x-ray, an electrocardiogram, allergy tests, etc. In a preferred embodiment of this invention, the pointer representation, as seen on the screen of the client workstation, is as seen in FIG. 6C. The textual representation of the pointer indicates clearly to the user the medical document or information to which the pointer points, whether it be the most recent or a previous electrocardiogram, coronarography, x-ray, or brain CT scan. Alternatively, the pointers may be of a graphical representation, small icons used to specify relevant body parts and illustrate medical treatments. The scope of this invention also includes all other variations of a pointer representation implementation which reveals the nature of the information to which it points. Transparent to the user is the actual address, hidden beneath the physical representation, which is the actual device needed for contacting and downloading from various external LANs and other sources, to be discussed in more detail below.

In short, the NDSMR record is a data structure that contains two types of elements, namely a collection of medical data elements about the individual and one or more pointers that allow additional information to be downloaded, this additional information being of a medical nature and complementing the data held in the collection of medical data elements. Specific to this invention, these pointers adopt the URL (Universal Resource Locator) addressing system, which allows pointing to a specific file in a directory, where that file and that directory can exist on any machine on the integrated health network and can be served via any of several different methods, specifically the Internet technologies such as ftp, http, gopher, etc. The URL addressing system is well documented and very well known to those skilled in the art, and therefore will not be described in more detail.

Each pointer provides an address which may consist in the entire address information of the file pointed to by the pointer or in a reference to the address information, where the reference may be an index in a table that contains the address information. Associated directly with the pointer is a data field, possibly stored in a mapping table in the memory of the NDSMR server, where this data field contains data indicative of the basic nature of the information held in the file or resource to which the pointer is directed. For the purposes of this specification, when used in the context of a pointer and a data field, the term "associated" means that the data field is either in a direct one-to-one mapping relationship with the pointer or, alternatively, is integrated with the pointer address to form the actual pointer data structure. In a very specific embodiment, the data field associated with the pointer, indicative of the basic nature of the information pointed to, can contain codes normally used by physicians to categorize treatment events that they have administered to patients. Those codes are normally used for remuneration purposes, however, they can be employed here in a satisfactory manner as indicators of the nature of the medical data. Alternatively, the data field associated with the pointer may also contain the date and time at which the pointer was created (enabling the display of the information at the client workstation to be effected in a chronological order), a textual description of the medical information pointed to, a brief description of the status/results of the medical information pointed to, etc.

To facilitate the reading of the information associated with the pointers, namely the basic nature of the medical data, the display of the pointers may be organized and enhanced to enable the user to easily grasp the meaning of the data without the necessity to refer to lists cross-referencing codes with the basic nature of the medical data. This can be accomplished in several ways. For instance, the pointers related to the same information, for instance containing the address of files that hold electrocardiograms, may be displayed on the client workstation in a separate window and arranged in that window in chronological order. Another possibility is to display beside each pointer an icon or text box with the suitable data. This can be accomplished by providing the client workstation with a table that maps the code in the pointer identifying the basic nature of the medical data with the type of information to be displayed to the user. When the NDSMR is loaded from the remote server 300, the list of pointers is identified and scanned to extract from them the codes identifying the basic nature of the medical data. The codes are then cross-referenced through the table with the corresponding information to be displayed. The information is then displayed on the screen of the user.

Another aspect of this invention is the update of the NDSMRs, following the creation of new medical data. This task could be effected by a NDSMR administrator, be it a medical archivist, webmaster, or some other administrative appointee, also responsible for the maintenance and regular update of a local medical information system. Taking for example the medical archivist, it is known that within all of the healthcare establishments such archivists are currently responsible for ensuring maintenance of all local medical files, as well as for producing hospitalization summaries, and therefore are aware of all recent medical acts and treatments performed within their medical facility. An alternative to the use of NDSMR administrators is the implementation of automatic NDSMR updates, a process which would involve the incorporation of some sort of intelligence system into all local medical network information systems.

Figure 9:
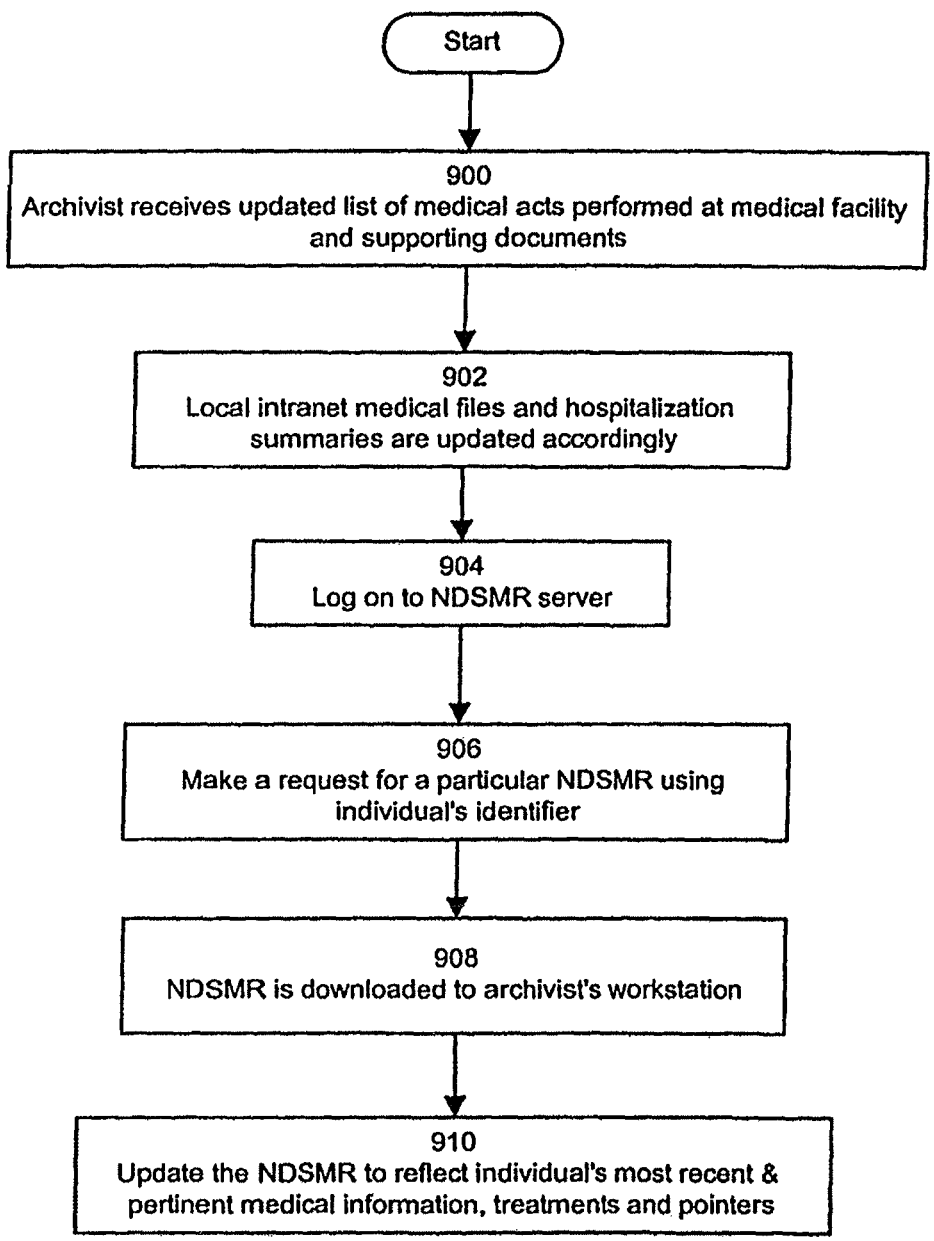
FIG. 9 is a flowchart of the update process performed by the archivists on the NDSMRs, in accordance with an example of implementation of the present invention.

FIG. 9 illustrates an example of a procedure to be followed by medical facility archivists in order to update the NDSMRs. Assume that the archivist within a particular medical facility receives on a regular basis, at step 900, a list of recent medical acts performed at the facility, as well as supporting documents for these acts. At step 902, the archivist updates the facility's local Intranet medical files and creates updated hospitalization summaries. The archivist's next step is to log on to the NDSMR server, using an archivist assigned password, at step 904. The server and its DBMS will recognize the archivist password and profile and assign privileges accordingly, as described above for steps 804 and 818 of the NDSMR server program element. For each different patient appearing on the archivist's updated list, a request must be made in order to retrieve the appropriate NDSMR. The request is made on the basis of the particular patient's identifier, submitted to the NDSMR server at step 906. At step 908, the NDSMR is downloaded to the archivist's workstation, at which point the archivist is capable of modifying and updating certain sections of the data contained in the NDSMR, for instance the Significant Antecedents, Current Medical Condition and Links To Other Biological Data categories as seen in FIG. 6C. At step 910, the archivist refers to the updated list to update the NDSMR in order to reflect the individual's most recent and pertinent medical information, treatments, and corresponding pointers. For example, assume that one of the archivist's list entries is that Mr. John Doe has undergone a new electrocardiogram at Hospital E. The archivist will then change the Most Recent Electrocardiogram reference seen in the Links To Other Biological Data category of Mr. Doe's NDSMR to point to the Hospital E local network, more particularly to the file containing the digitized electrocardiogram.

It is important to note that in order for the NDSMR system to function within an extended network of LANs or local Intranets, all documents referred to by pointers should be archived according to a specific nomenclature and be accessible outside of the LAN. In a most preferred embodiment of this invention, this specific nomenclature consists of that adopted by a state or national medical insurance company, thus ensuring record consistency and successful searches. The pointer addresses, transparent to the user, must also have a specific structure, to be respected by all archivists. In a most preferred embodiment of this invention, the structure of the pointer addresses, all the while respecting the URL addressing system, consists of a combination of a local network and machine address (or domain name), a patient's identifier, and a code taken from a published manual of medical act codes adopted by a state or national medical insurance company. There do exist alternatives to the specific nomenclature and pointer structure used by the NDSMR system, and the scope of this invention includes all other such variations whereby consistency is assured within the system.

Yet another feature of this invention is its use as a search/query engine. Not only can a user perform searches for or queries on NDSMRs within his/her own local Intranet, but also within external sources. NDSMR searches and queries may be performed on two different types of data, and therefore databases: nominative and non-nominative. Non-nominative medical data and databases are accessible to all authorized users, but do not require authorization from the patient whose personal data is being consulted. Nominative medical data and databases require search authorization from both the workstation client, typically a doctor or consultant, and the concerned patient, with the exception of situations where emergency medical care is required. The search requester will be prompted for this authorization through the workstation interface described above, the authorization comprising some form of password, biological signature, or smart card. In the case where a search is performed by a user without nominative search authorization, the NDSMR Database Management System (DBMS) will automatically mask any nominative data found in the database response before transmitting it to the client workstation. In summary, the NDSMR system permits the delay-free consultation of pertinent information found within different local files and, for authorized users, offers an integrated research motor which allows for non-nominative research, by object or by concept, on the whole of the accessible databases.

In a specific example, a user of the NDSMR system may perform a search of all of the non-nominative medical data and databases accessible via the server 300 for a particular genetic characteristic. Thus, the search results returned to the user by the NDSMR system in response to this query would comprise all NDSMRs, both local and external to the user's Intranet, containing non-nominative medical data that share this particular genetic characteristic. As mentioned above, all nominative data within these NDSMRs would be masked by the NDSMR DBMS before transmission of the query response to the client workstation. Advantageously, on a basis of such a query it may be possible to associate one or more health problems or medical conditions experienced by a known population with a particular genetic characteristic shared by the known population, thus furthering medical research.

For the purposes of the present description, the expression "medical condition" means a state of health of an individual, and may include a disease with which the individual is afflicted as well as a medical trait or a medical characteristic proper to the individual. In a specific example, the medical condition found to be associated with a genetic characteristic is a medical disease, such as Alzheimers, diabetes, or depression, among many other possibilities. Alternatively, the medical condition may be a particular cholesterol level, a particular blood pressure level, or a particular body mass index, among many other possibilities.

In a preferred embodiment of the invention, the NDSMR includes genetic data for the respective individual, allowing elaborate genetic research to be conducted by a user of the NDSMR system. In a specific example, the genetic data are stored in the NDSMR database and maintained by the NDSMR server. More specifically, one or more medical data elements of the summary medical record consist of genetic data. Alternatively, the genetic data are stored remotely from the NDSMR server, in one or more different local networks. In the latter case, one or more pointers of the NDSMR provide links to the remotely stored genetic data, allowing a user of the NDSMR system to download and access the genetic data.

In yet another alternative, genetic data for a respective individual are neither stored in the NDSMR database nor maintained by the NDSMR server. Rather, the genetic data are stored in one or more electronic databases containing records for a plurality of individuals, where the one or more electronic databases are separate from the NDSMR system but are designed such that the records are indexed using the same unique identifiers as those used by the NDSMR system. Each record of such an electronic database stores genetic data associated with a respective individual, and possibly other medical information for the same individual. As in the case of the unique identifier in the NDSMR medical records, the unique identifier in the electronic database distinguishes one individual's record from another and is used to access the information for a particular individual. Examples of unique identifiers include an individual's biological signature, medical insurance number, social insurance number, and Smart Card. Similarly to the NDSMRs, the records of these one or more separate electronic databases are regularly updated, such that each record includes a compendium of genetic data for the associated individual.

In the latter case, when the genetic data for an individual are stored in an electronic database that is separate from the NDSMR system, genetic research performed by a user would include querying both the NDSMR system and the electronic database. In a possible example, the user would first submit a query to the NDSMR system for the NDSMRs associated with all individuals afflicted with a particular health problem. Next, the user would retrieve from the electronic database the genetic data for all of the particular individuals identified by the first query of the NDSMR system, on the basis of the unique identifiers of these particular individuals.

Advantageously, since the NDSMR system maintains and provides supporting diagnostic information, such as electrocardiogram, coronarography, x-ray, brain CT scan, or allergy tests, in addition to actual diagnosed medical conditions for each patient, the NDSMR system allows for conclusive genetic research results, as opposed to the more common preliminary or probable results. More specifically, a genetic research study may be conducted not only on the basis of patients' genetic data and diagnosed medical conditions, but also on the basis of supporting diagnostic information, which leads to a more exhaustive study and more accurate conclusions.

It should be noted that the above-described NDSMR system is but one example of a system and method for electronically managing medical data in order to facilitate genetic research on this medical data. Simply put, any electronic database modeled after the NDSMR database, or any health Intranet providing distributed medical information that is modeled after the NDSMR system, will facilitate complex genetic research. As long as, for each individual, the electronic medical data management system includes at least one universal or network-attributed identifier, medical information pertinent to the individual, and genetic data pertinent to the individual, the electronic medical data management system will provide enhanced genetic research capabilities.

Such an electronic database or health Intranet may include a medical record database similar to the NDSMR database, where each medical record necessarily includes at least one universal or network-attributed identifier distinguishing one record from another, genetic data, and medical information pertinent to the individual associated with the record. Alternatively, the genetic data may be stored remotely from the medical records, in a separate dedicated or non-dedicated electronic database, indexed by the same identifiers as used within the electronic database or health Intranet. The medical information stored in the medical record may be in the form of:

textual data;
textual data and a dynamically updated list of biological data pertinent to the individual;
textual data and graphical data; and
textual data and multimedia information,
among other possibilities.

As in the case of the NDSMR system, the biological data may consist of significant medical documents in an electronic format, such as laboratory tests, x-rays, surgical reports, electrographic data, etc., which provide supporting diagnostic information. In a specific example, this biological data is accessible by one or more pointers stored in the medical record, where these pointers address one or more remote databases where the data are actually being stored.

Many different formats of genetic data exist and may be used by the NDSMR system or any other health Intranet or electronic database without departing from the scope of the present invention. Examples of possible formats for the genetic data stored in or accessible by the NDSMR or any other health Intranet or electronic database include the following four formats:

1) Entire Sequence or Segment(s) of Chromosomal and/or Mitochondrial Genome

As is well known, the genome of an organism is defined as all genetic information or hereditary material possessed by an organism. In humans and other higher life forms, the total genome is made up of both the chromosomal genome and the mitochondrial genome. Whereas the chromosomal genome is genetic information found within chromosomes inside the nucleus of a cell, the mitochodrial genome is genetic information found within mitochondrial chromosomes outside the nucleus of a cell.

2) Single Nucleotide Polymorphisms (SNPs)

The majority of the DNA sequence variation responsible for human variation in the genome is due to a limited number of common variants known as SNPs. Polymorphisms are differences in the genomic DNA sequences that naturally occur in a population. SNPs are particular DNA sequence variations that occur when a single nucleotide (A, T, C, or G) in the genome sequence is altered. Such variations can be used to track inheritance in families.

3) SNP Haplotypes or SNP Haplotype Tags

SNPs have been estimated at 10,000,000 in the human genome, or one per 300 genome base pair (bp). But not all possible combinations of SNPs occur in humans. Findings suggest that variations are not uniformly distributed in the genome; rather variations may occur in blocks with clustering of variations into common subtypes. SNP haplotypes consist of a grouping of SNPs in linkage on a chromosomal segment, and have the potential to capture the majority of the variations present within and between human populations. A minimal selection of SNPs that have the most discrimination power for haplotype identification are named haplotype tagging SNPs or htSNPs. Because of the linear nature of DNA, the variation observed at SNP haplotypes is determined by recombination events along chromosomes and by the historical filial structure of human populations.

It is possible to retain much of the information of haplotypes by retaining only a reduced subset of markers. If the haplotype structure is identified across the genome, and if one marker is studied for each haplotype, then it will not be necessary to test all 10,000,000 common variants. In fact, haplotype tagging SNPs have the potential to reduce the total number of informative genomewide SNPs from 10,000,000 to approximately 500,000 informative tags. The reduction in the number of information tags therefore enables substantial information compression, and can facilitate the analysis of genetic susceptibility to common medical diseases.

4) Polymorphic Markers

A polymorphic marker displays variability in the population, thereby allowing its inheritance to be followed. In general, a genetic marker is a segment of DNA at a known physical location on a chromosome, such as VNTRs (Variable Number of Tandem Repeats). The marker can be used to track the inheritance pattern of genes that have not yet been identified, but whose approximate locations can be inferred using the markers.

In a specific, non-limiting example of implementation, an adaptive expert system is used in conjunction with the NDSMR system for performing genetic research on the basis of medical and genetic data stored in the NDSMR database. Typically, an association model is first developed by the adaptive expert system, for the purposes of determining an association that may exist between the stored genetic data and a medical condition. Next, the adaptive expert system is capable of evaluating the possible contribution of any genetic data added to the NDSMR database under a new data field. Thus, by evaluating the medical and genetic data stored in the NDSMR database using an association model, data analysis not normally achievable can be effected. Since the functionality and different possible implementations of such an adaptive expert system have been well documented and are well known to those skilled in the art, they will not be described in further detail in this document.

Note that the adaptive expert system may be integrated into the NDSMR server or, alternatively, may be implemented as a stand-alone system in communication with the NDSMR server. In the case where genetic data are stored and maintained by one or more electronic databases separate from the NDSMR system but indexed using the same unique identifiers as the NDSMR system, the adaptive expert system would be used in conjunction with both the NDSMR system and the separate electronic databases for performing the genetic research.

It should also be noted that a similar relationship between an adaptive expert system and the medical record database(s) can be conceived for the different possible types of electronic medical data management systems described above (i.e. health Intranet, electronic database, etc.).

As is well known, association models for adaptive expert systems are built using statistical association methods. In the context of the present invention, association methods may be used to associate health problems with genetic characteristics that are shared by an affected population. One possible method for developing an integrated expert system for association testing is by the use of an artificial neural network (ANN).

As is well known to those skilled in the art, ANNs are computational tools modeled on the biological nervous system with multifactorial mathematic modeling properties that can be used for the purposes of classification, prediction, function estimation, and pattern recognition by capturing and representing complex input/output relationships. More specifically, artificial neural networks are digitized models trained by processing a large number of input patterns and being shown the output pattern that resulted from each corresponding input pattern. The ANN therefore learns how to recognize data patterns such that, once trained, the ANN is able to produce a predicted output pattern whenever it is presented with a new input pattern never encountered before. This is especially useful in the area of genetic research where there may be a large amount of data to analyze, and data patterns are not as apparent.

Structurally, the ANN consists of nodal processing elements that act in parallel. Inspired by biological nervous systems, the processing elements are called neurons, while layered networks of the neurons are called neural networks. In a simple neural network, neurons are organized into at least three different layers: the input layer, one or more hidden layers, and the output layer. The input layer receives the input, such as data from the NDSMR database. The output layer produces the final output or target of interest in the test of association, such as disease outcome. One or more hidden layers are found between the input layer and the output layer, and are modeled by training the neural network. The neurons or processing elements in the ANN are connected to each other by weighted coefficients. Therefore, the processing elements in a particular layer depend on the data received from the processing elements in the previous layer and the weights on the connections between these two layers.

Neural networks have been extensively developed and applied as a supplement or alternative to standard statistical techniques, with some considerable advantages. Neural networks inherently allow for arbitrary nonlinear relations between independent and dependent variables and can therefore model all possible interactions between variables. Standard statistical approaches, such as logistic regression or Cox regression, would require extensive modeling to allow such interactions.

Hence, artificial neural networks are well suited to model and test associations using the data fields of the NDSMR database. In an illustrative example, inputs to the neural network are obtained from the NDSMR database and may include genetic variables (such as SNPs), environmental factors (such as smoking status, age), or medical factors (such as medications, interventions). The outputs used to train the neural network may include health status information, such as medical traits and diagnosed diseases. In a specific example, the health status information includes the status of an individual with regard to cholesterol level. In another example, the health status information includes the status of an individual with regard to cardiovascular disease. Essentially, selected medical and genetic data of an individual are provided as input, and a status of whether or not the individual possesses a particular medical trait or is afflicted by a particular medical disease is used as corresponding output. A plurality of such input and output data must be provided in order to train the artificial neural network. The ANN is trained to predict a medical condition outcome, such as cardiovascular disease or high cholesterol, such that a hypothesis-based neural network model can be developed. Thus, in a specific, non-limiting example, a predictive value of neural net inputs could be tested for association to cardiovascular disease using the hypothesis-based neural network model.

An adaptive expert system may use any suitable association method, including epidemiological studies and artificial neural networks, in conjunction with the NDSMR system for performing genetic research on the basis of medical and genetic data stored in the NDSMR database. The adaptive expert system would include a mathematical model built from ANN or using principal component statistics. The association model would allow testing of, for example, genetic factors, proteomic factors, viral infection history, environmental factors, gene therapy, and cell or tissue grafts (allografts, autografts, or stem cell grafts) with specific disease manifestations. Such associations may well provide genetic markers for laboratory tests, as well as specific targets (genetic, proteomic, or cell targets) for therapeutic interventions including pharmacotherapeutics.

In a specific example, the adaptive expert system could be used to automatically identify any significant contributions of newly introduced genetic data (SNP, SNP haplotype, or marker or polymorphic marker), added to the NDSMR database under a new data field. The adaptive expert system would automatically evaluate the potential contribution to active and previously defined ANN association models. Hence, it would be possible to validate some new correlation not previously assessed, and there would be potential for new diagnostic or therapeutic tools.

Figure 10:
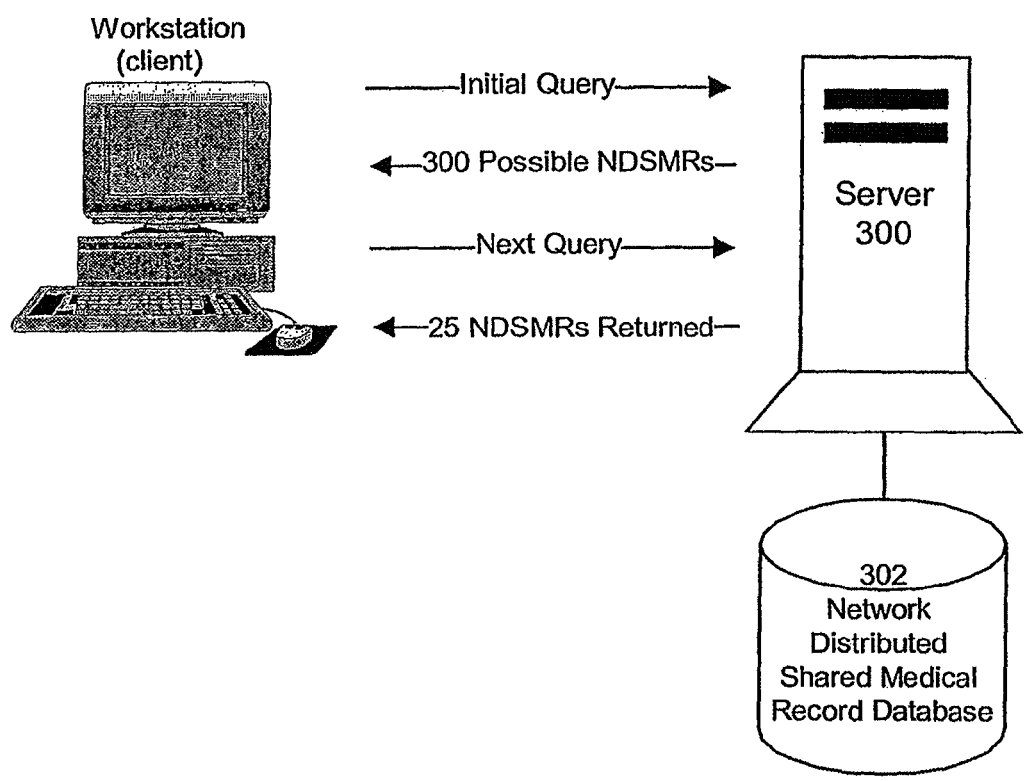
FIG. 10 is a block diagram of the search engine (query) process implemented by the NDSMR system, in accordance with an embodiment of the present invention.

FIG. 10 displays the query usage allowed by the NDSMR system. From a client workstation, a user may make an initial query of the server 300. The server's DBMS and database logic allow the NDSMR database 302 to be searched rapidly and efficiently. The database logic is what allows the server to not only retrieve records on behalf of the client but also to perform searches on behalf of the client. We see in FIG. 10 that an initial query returned 300 possible NDSMRs. The system allows the user to send out a second, more narrow query, with a resulting 25 NDSMRs returned. The system is therefore very efficient, especially for massive searches performed across all accessible databases. In a most preferred embodiment of this invention, the query style offered by the workstation interface will be one of relational data searches, such as the style currently offered by the Alta Vista™ web browser. The query style will not be described in detail as it is very well known to a person skilled in the art. Alternatively, many other query styles could be incorporated into the NDSMR search engine, for instance an object-oriented search style.

The structure of the pointers as described above, where both an address part and an associated data part form a pointer, allows the NDSMR system to perform searches on all of the pointers contained within the NDSMR database, representing medical files archived at all of the various local networks connected within the extended health network. As mentioned above, the data structure of the pointers allows the nature of the information to which they point to be determined, either directly from the data structure itself in the case where both the data part and address part of the pointer are integrated to form the data structure of the pointer, or through a one-to-one mapping between the address part of the pointer's data structure and the data part, possibly stored in a mapping table in the memory of the NDSMR server. Consequently, medical searches performed on the NDSMRs will return all database records containing pertinent pointer links. These links will allow the user to research medical data from all over the health network, currently impossible but vital to progressive medical development. Thus, a query could be made to extract records based on a key relating to the basic medical information. For example, one could extract the records of all individuals between the ages of 25-35 that have undergone a particular therapy. This information is particularly useful in statistical studies.

As mentioned above, the use of a Smart Card as a unique network validated or attributed identifier for users of the NDSMR system offers several implementation alternatives to the system. In a specific alternative embodiment of the invention, the Smart Card can be used at the client workstation in order to access the NDSMR database. For example, upon attempting to log onto the NDSMR system, the client, most likely a physician, will be prompted by the NDSMR system server (through the user-friendly interface seen at the workstation) to insert the patient's Smart Card into the workstation's appropriate electronics. The electronics read the information contained on the card and can extract the patient's identification. The NDSMR server's program element then passes control to its validation functional block in order to ensure that the patient is a server-registered user, as described above. In another example, the NDSMR system server may prompt the client workstation user for two Smart Cards, both the physician's and the patient's, thereby increasing the security of the system.

The Smart Card may provide more than simple user identification. In another alternative embodiment of the invention, a patient's Smart Card contains medical information specific to the patient. In one example, the NDSMR system includes the Smart Card as a storage medium for system user information, with the NDSMR database records consisting strictly of at least one unique identifier and a dynamically updated list of pointers to relevant medical information located at remote locations. In such a system, the patient's Smart Card would contain all other medical information pertinent to the individual, for instance that shown in FIGS. 6A, 6B, and 6C (minus the Links To Other Biological Data). Upon logging in to the NDSMR system with a Smart Card (or two), the medical information stored on the patient's Smart Card would appear on the client workstation, along with the list of pointers downloaded from the patient's record in the NDSMR database. In another example, a patient's nominative information could all be stored on the Smart Card, with only the patient's non-nominative information stored in the NDSMR database along with the identifier(s) and the list of pointers. This particular implementation of the system would ensure that no queries/searches performed on the NDSMR database revealed any confidential, nominative patient information.

A patient's Smart Card, or alternatively any other form of portable computer-readable storage medium, may also be used to store and maintain all or a portion of the data found in the particular patient's NDSMR, where this data may be nominative, non-nominative, static, or dynamic. In such a situation, the NDSMR server offers a continuously available way to update the Smart Card, the update consisting of reading the latest information from the NDSMR and writing it to the Smart Card via the appropriate electronics, without changing any of the static or nominative data stored on the card. This implementation would allow a physician, at a hospital external to the NDMSR system's integrated health network, to have access to the individual's pertinent and most recent medical information, the only requirement being that the hospital must have the appropriate electronics to read the individual's Smart Card.

A variety of other NDSMR system implementations also exist, distributing the whole of the patients' medical information between database records and patient Smart Cards or other such portable computer-readable storage media, and are included within the scope of this invention.

In yet another example of implementation, a personal communication system (PCS), such as a cellular phone, can be used to access the NDSMR database. Other examples of such a PCS include a web phone, a cellular notepad, an IP television screen or monitor, among others. In this example of implementation, users of the NDSMR system, including patients that are registered with the NDSMR system as well as healthcare professionals, can benefit from convenient, mobile mechanisms for accessing and using the NDSMR system.

In this non-limiting example of implementation, the PCS is equipped with the same communication exchange protocol as that in use by the NDSMR server 300, such that a connection may be established between the PCS and the NDSMR server 300. This communication exchange protocol may be the Internet Protocol, or any other similar progressive communication exchange protocol.

As described above, when a client attempts to log into the NDSMR system, the NDSMR server 300 will perform a validation procedure in order to confirm that the client is a registered user of the NDSMR system. In one specific example, this validation procedure consists of the server 300 prompting the user of the PCS for an ID and password that are authenticated by the server 300 on the basis of the validation table. Examples of such an ID include a medical insurance number, a social insurance number, a Smart Card, a network-attributed identifier, as well as a digital print of the user or any other type of biologically derived signature.

In another specific example, the PCS provides, or itself acts as, an authentication key to uniquely identify a particular user. In the case of a cellular phone, each cellular phone includes a microchip that may serve as the authentication key. For example, when the cellular phone connects to the NDSMR server 300, the microchip will append to the request for connection a unique signature, recognizable by the server 300 as being associated with a registered user of the NDSMR system. Alternatively, the authentication key may be a unique signature of the microchip validated by a PIN number, where the server 300 will prompt the user of the PCS for this PIN number, or any other method of singular identification.

In addition to an authentication key, the PCS provides the user with a display over which the user may view medical information and query the NDSMR system. In a specific example, the above-described user-friendly interface is provided by the server 300 to the display of the PCS, where this interface permits the PCS user to make data requests, perform searches or queries on the NDSMR database, and perform keyword-based Internet-wide searches, among other options. In the case of a cellular phone, the screen of the cellular phone provides a medium over which a certain amount of information can be displayed. Where a large amount of medical information is to be requested of the NDSMR system by the user, the cellular phone may be linked to a television monitor or to a personal or professional computer workstation, for providing the user with a more appropriate amount of display area.

As in the case of the Smart Card, a PCS of a patient registered with the NDSMR system may include a memory device that contains medical information specific to the patient. In one example, the NDSMR system includes the memory device of the PCS as a storage medium for system user information, with the NDSMR database records consisting strictly of at least one unique identifier and a dynamically updated list of pointers to relevant medical information located at remote locations. In such a system, the patient's PCS would contain, in its memory device, all other medical information pertinent to the individual. When a patient logs in to the NDSMR system via his/her PCS, the medical information stored in the patient's PCS would appear on the PCS display, along with the list of pointers downloaded from the patient's record in the NDSMR database. In another example, a patient's nominative information could all be stored in the memory device of the PCS, with only the patient's non-nominative information stored in the NDSMR database along with the identifier(s) and the list of pointers. This particular implementation of the system would ensure that no queries/searches performed on the NDSMR database revealed any confidential, nominative patient information.

In a specific, non-limiting example, the microchip of a cellular phone belonging to a patient registered with the NDSMR system is used as a storage medium to store and maintain all or a portion of the data found in the particular patient's NDSMR, where this data may be nominative, non-nominative, static, or dynamic. The data stored on the microchip may be updated on a request basis where, pursuant to logging in to the NDSMR system, a request is sent from the cellular phone to the NDSMR server for updating of the data being maintained on the microchip of the phone. Alternatively, the data stored on the microchip may be updated automatically whenever new pertinent medical information for the particular patient has been archived on the NDSMR server. Specifically, the NDSMR server 300 can offer a continuously available mechanism to update all of the cellular phone users having subscribed to such a service either directly, through their medical insurance company, or through a medical plan under which they are protected.

Taking the example of a cellular phone user that has subscribed to the service directly, when the server 300 is performing the automatic update it will read the latest medical information from the patient's NDSMR and will transmit this data to the patient's cellular phone. In order to perform the data transmission, the server 300 will first attempt to establish a connection with the patient's cellular phone. Once a connection is established, the server 300 will transfer the pertinent medical information to the microchip of the cellular phone, without changing any of the static or nominative data stored in the microchip.

Note that, in addition to being used as a way to access the NDSMR system, a PCS may also be used to access any health Intranet that provides distributed medical information and offers to registered users of the Intranet the possibility of connecting via a PCS. Such a health Intranet may include a summary medical record database similar to the NDSMR database, where each summary medical record necessarily includes at least one universal or network-attributed identifier, distinguishing one record from another, as well as medical information pertinent to the individual associated with the record. This medical information may be in the form of:
- textual data;
- textual data and a dynamically updated list of biological data pertinent to the individual, accessible by one or more pointers addressing one or more remote databases where the data are actually being stored; and
- textual data and multimedia information,
- among other possibilities.

As in the case of the NDSMR system, the biological data that are accessible by pointers may consist of significant medical documents in an electronic format, such as laboratory tests, x-rays, surgical reports, electrographic data, etc.

The above detailed description of examples of implementation under the present invention should not be read in a limitative manner as refinements and variations are possible without departing from the spirit of the invention. The scope of the invention is defined in the appended claims and their equivalents.

Although the invention is illustrated and described in this document with reference to specific embodiments, the invention is not intended to be limited to the details shown. Rather, various modifications may be made in the details within the scope and range of equivalents of the claims and without departing from the invention.

What is claimed:

1. In a data communication system, a method for updating medical information, the data communication system comprising:
    (a) network server arrangement in which is stored a medical record of a user;
    (b) a mobile cellular telephone including machine readable storage and a display, the machine readable storage containing a medical file of the user, which can be displayed by the display, the method for updating medical information including:
        i. transmitting data conveying new medical information about the user to the network server arrangement and storing the data in the medical record of the user;
        ii. initiating by the network server arrangement a communication with the mobile cellular telephone when the data conveying the new medical information has been stored on the network server arrangement;
        iii. transferring to the mobile cellular telephone at least a portion of the data conveying the new medical information;
        iv. storing in the machine readable storage at least a portion of the data conveying the new medical information to update the medical file of the user.

2. A method as defined in claim 1, wherein the machine readable storage stores nominative information about the user.

3. A method as defined in claim 1, wherein the machine readable storage stores a name of the user.

4. A method as defined in claim 1, wherein the machine readable storage stores a telephone of the user.

5. A method as defined in claim 1, wherein the machine readable storage stores emergency contact information of the user.

6. A method as defined in claim 1, wherein the machine readable storage stores a date of birth of the user.

7. A method as defined in claim 1, wherein the machine readable storage stores a blood type of the user.

8. A method as defined in claim 1, wherein the machine readable storage stores information about a genetic marking of the user.

9. A method as defined in claim 1, wherein the machine readable storage stores information about a genetic deficiency of the user.

10. A method as defined in claim 1, wherein the machine readable storage stores information about tissue antigens of the user.

11. A method as defined in claim 1, wherein the machine readable storage stores information about medication prescribed to the user.

12. A method as defined in claim 1, wherein the machine readable storage stores information about allergies from which the user is suffering.

13. A method as defined in claim 1, wherein the machine readable storage stores information about past hospitalizations of the user.

14. A method as defined in claim 1, wherein the machine readable storage stores information about therapeutic treatments to which the user has been subjected.

15. A method as defined in claim 1, wherein the machine readable storage stores information about a surgery to which the user has been subjected.

16. A method as defined in claim 1, wherein the machine readable storage stores information about a radiology procedure to which the user has been subjected.

17. A method as defined in claim 1, wherein the storing in the machine readable storage of the at least a portion of the data conveying the new medical information to update the medical file of the user, is performed without changing at least a portion of the existing data in the machine readable storage.

18. A mobile cellular telephone for storing medical information about a user of the cellular telephone, the cellular telephone comprising:
    (a) machine readable storage containing medical information about a user of the mobile cellular telephone;
    (b) a display;
    (c) the mobile cellular telephone being responsive to a request sent over a data communication pathway initiated by a network server arrangement storing updated medical data for the user, for updating the medical information stored in the machine readable storage, the updating including:
        (i) receiving new medical data and storing the new medical data in the machine readable storage to update the medical information about the user;
        (ii) the updated medical information in the machine readable storage being viewable on the display.

19. A mobile cellular telephone as defined in claim 18, wherein the machine readable storage stores nominative information about the user.

20. A mobile cellular telephone as defined in claim 18, wherein the machine readable storage stores a name of the user.

21. A mobile cellular telephone as defined in claim 18, wherein the machine readable storage stores a telephone of the user.

22. A mobile cellular telephone as defined in claim 18, wherein the machine readable storage stores emergency contact information of the user.

23. A mobile cellular telephone as defined in claim 18, wherein the machine readable storage stores a date of birth of the user.

24. A mobile cellular telephone as defined in claim 18, wherein the machine readable storage stores a blood type of the user.

25. A mobile cellular telephone as defined in claim 18, wherein the machine readable storage stores information about a genetic marking of the user.

26. A mobile cellular telephone as defined in claim 18, wherein the machine readable storage stores information about a genetic deficiency of the user.

27. A mobile cellular telephone as defined in claim 18, wherein the machine readable storage stores information about tissue antigens of the user.

28. A mobile cellular telephone as defined in claim 18, wherein the machine readable storage stores information about medication prescribed to the user.

29. A mobile cellular telephone as defined in claim 18, wherein the machine readable storage stores information about allergies from which the user is suffering.

30. A mobile cellular telephone as defined in claim 18, wherein the machine readable storage stores information about past hospitalizations of the user.

31. A mobile cellular telephone as defined in claim 18, wherein the machine readable storage stores information about therapeutic treatments to which the user has been subjected.

32. A mobile cellular telephone as defined in claim 18, wherein the machine readable storage stores information about therapeutic treatments to which the user has been subjected.

33. A mobile cellular telephone as defined in claim 18, wherein the machine readable storage stores information about a surgery to which the user has been subjected.

34. A mobile cellular telephone as defined in claim 18, wherein the machine readable storage stores information about a radiology procedure to which the user has been subjected.

35. A mobile cellular telephone as defined in claim 18, wherein the storing of the new medical data in the machine readable storage to update the medical information about the user, is performed without changing at least a portion of the existing data in the machine readable storage.

36. A network server arrangement, comprising:
(a) a processor;
(b) a machine readable storage encoded with software for execution by the processor to service a request by a workstation client that is physically remote from the network server arrangement and communicates with the network server arrangement via a data link;
(c) the network server arrangement being responsive to a request by the workstation client to access a medical record of an individual for generating a response, the response including:
 (i) a summary information component, the summary information component including a plurality of data elements associated with the individual at last one of the data elements conveying medical information about the individual;
 (ii) a pointers component including at least one pointer that points to a network location containing importable medical information about the individual, the pointer including;
 (iii) a machine readable address part for processing by the workstation client, to allow the workstation client to import the medical information from the network location;
 (iv) a label part for displaying to a user at the workstation client the nature of the medical information residing at the network location;
(d) wherein the machine readable storage is a first machine readable storage and the network server arrangement stores medical records of a plurality of individuals, the network server arrangement being configured for:
 (i) in response to reception of data conveying new medical information about a user that has a medical record stored in the network server arrangement, establishing a communication session with a mobile cellular telephone of the user;
 (ii) transferring to the mobile cellular telephone at least a portion of the data conveying the new medical information for storage in a machine readable storage on the mobile cellular telephone for updating medical information about the user stored on the mobile cellular telephone.

\* \* \* \* \*